United States Patent [19]

Campbell et al.

[11] Patent Number: 4,572,908

[45] Date of Patent: Feb. 25, 1986

[54] DIHYDROPYRIDINES

[75] Inventors: Simon F. Campbell, Deal; Peter E. Cross, Canterbury; John K. Stubbs; John E. Arrowsmith, both of Deal, all of England

[73] Assignee: Pfizer Inc., New York, N.Y.

[21] Appl. No.: 562,482

[22] Filed: Dec. 16, 1983

[30] Foreign Application Priority Data

Dec. 21, 1982 [GB] United Kingdom ............... 8236347

[51] Int. Cl.[4] ............... C07D 401/12; C07D 403/12; A61K 31/44

[52] U.S. Cl. .................... 514/340; 514/342; 514/255; 514/269; 514/272; 514/274; 514/318; 546/256; 546/276; 546/277; 546/278; 546/270; 546/280; 544/320; 544/333; 544/405; 544/114; 544/198; 544/317; 544/310; 544/277; 544/284; 544/131; 544/124; 544/258

[58] Field of Search ............... 546/276, 277; 424/266

[56] References Cited

U.S. PATENT DOCUMENTS

| 4,144,343 | 3/1979 | Baldwin et al. | 424/263 |
|---|---|---|---|
| 4,284,634 | 8/1981 | Sato | 424/266 |
| 4,430,333 | 2/1984 | Campbell et al. | 424/266 |

FOREIGN PATENT DOCUMENTS

| 0031801 | 7/1981 | European Pat. Off. . |
| 0060674 | 9/1982 | European Pat. Off. . |
| 0089167 | 9/1983 | European Pat. Off. . |
| 2658183 | 7/1978 | Fed. Rep. of Germany . |
| 2740080 | 3/1979 | Fed. Rep. of Germany . |
| 2844595 | 4/1980 | Fed. Rep. of Germany . |
| 3022030 | 12/1981 | Fed. Rep. of Germany . |
| 55-47656 | 4/1980 | Japan . |
| 1585978 | 3/1981 | United Kingdom . |

OTHER PUBLICATIONS

Fossheim et al., CA 96:52141y.
Meyer et al., CA 95:143841x.
Deme et al., CA 96:68160x.
Wamhoff et al., CA 96:217781x.
Meyer et al., CA 88:120947c.
Kastron et al., CA 91:91466b.
Aritomi et al., CA 94:156797n.
Dainippon Pharmaceutical Co., CA 94:15570a.

Primary Examiner—Jane T. Fan
Attorney, Agent, or Firm—Charles J. Knuth; Albert E. Frost; James M. McManus

[57] ABSTRACT

Dihydropyridine anti-ischaemic agents of the formula:

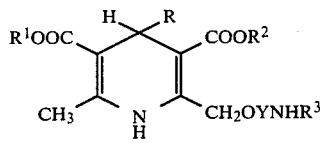

and their salts where R is aryl or heteroaryl, $R^1$ and $R^2$ are each $C_1$-$C_4$ alkyl or 2-methoxyethyl, Y is —$(CH_2)_n$— where n is 2, 3, or 4 and is optionally substituted by 1 or 2 $CH_3$ groups, and $R^3$ is an optionally substituted 5- or 6-membered heterocyclic group attached to the adjacent N atom by a C atom, said group $R^3$ being optionally fused to a further heterocyclic group or to a benzene ring.

14 Claims, No Drawings

DIHYDROPYRIDINES

BACKGROUND OF THE INVENTION

This invention relates to certain dihydropyridines, specifically to certain 1,4-dihydropyridines having a heterocyclic group in a side chain attached to the 2-position, which have utility as anti-ischaemic and anti-hypertensive agents.

The compounds of the invention reduce the movement of calcium into the cell and they are thus able to delay or prevent the cardiac contracture which is believed to be caused by an accumulation of intracellular calcium under ischaemic conditions. Excessive calcium influx during ischaemia can have a number of additional adverse effects which would further compromise the ischaemic myocardium. These include less efficient use of oxygen for ATP production, activation of mitochondrial fatty acid oxidation and possibly, promotion of cell necrosis. Thus the compounds are useful in the treatment or prevention of a variety of cardiac conditions, such as angina pectoris, cardiac arrythmias, heart attacks and cardiac hypertrophy. The compounds also have vasodilator activity since they can inhibit calcium influx in cells of vascular tissue and they are thus also useful as antihypertensive agents and for the treatment of coronary vasospasm.

SUMMARY OF THE INVENTION

Thus according to the invention there are provided dihydropyridines of the formula:

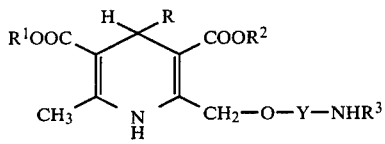
(I)

and their pharmaceutically acceptable acid addition salts;
wherein
R is an optionally substituted aryl or heteroaryl group;
$R^1$ and $R^2$ are each independently $C_1$-$C_4$ alkyl or 2-methoxyethyl;
Y is —$(CH_2)_n$— where n is 2, 3 or 4 and is optionally substituted by 1 or 2 methyl groups; and
$R^3$ is an optionally substituted 5- or 6-membered heterocyclic group attached to the adjacent nitrogen atom by a carbon atom, said heterocyclic group being optionally fused to a further 5- or 6-membered heterocyclic group or to a benzene ring, said further heterocyclic group and benzene ring also being optionally substituted.

The pharmaceutically acceptable acid addition salts of the compounds of the formula (I) are those formed from acids which form non-toxic acid addition salts, for example the hydrochloride, hydrobromide, sulphate or bisulphate, phosphate or acid phosphate, acetate, citrate, fumarate, gluconate, lactate, maleate, succinate and tartrate salts.

The term "aryl" as used in this specification includes unsubstituted phenyl and phenyl substituted by, for example, one or two substituents each independently selected from nitro, halo, $C_1$-$C_4$ alkyl, $C_1$-$C_4$ alkoxy, hydroxy, trifluoromethyl, and cyano. It also includes 1- and 2-naphthyl.

"Halo" means F, Cl, Br or I.

The term "heteroaryl" as used in this specification for R means an aromatic heterocyclic group which may optionally be substituted and includes, for example, benzofuranyl; benzothienyl; pyridyl optionally monosubstituted by methyl or cyano; quinolyl; benzoxazolyl; benthiazolyl; furyl; pyrimidinyl; thiazolyl; 2,1,3-benzoxadiazol-4-yl; 2,1,3-benzthiadiazol-4-yl; and thienyl optionally monosubstituted by halo or $C_1$-$C_4$ alkyl.

Alkyl and alkoxy groups having 3 or more carbon atoms can be straight or branched chain.

R is preferably phenyl substituted by 1 or 2 substituents selected from halo and $CF_3$. R is more preferably 2-chlorophenyl, 2,3-dichlorophenyl or 2-chloro-3-trifluoromethylphenyl. R is most preferably 2,3-dichlorophenyl.

Preferably either $R^1$ is $CH_3$ and $R^2$ is $C_2H_5$ or $R^1$ is $C_2H_5$ and $R^2$ is $CH_3$. Most preferably, $R^1$ is $CH_3$ and $R^2$ is $C_2H_5$.

Y is preferably —$(CH_2)_2$—.

$R^3$ is preferably a nitrogen-containing heterocyclic group.

$R^3$ is more preferably either (a) a monocyclic 5- or 6-membered heterocycle containing at least one N atom and optionally one or two further heteroatoms or groups each independently selected from O, S,

N, and

and is optionally substituted by $C_1$-$C_4$ alkyl, $C_1$-$C_4$ alkoxy, halo, hydroxy, oxo, cyano, 3-($C_1$-$C_4$ alkyl)ureido, phenyl, phenoxy, pyridyl, acetyl, ($C_1$-$C_4$ alkoxy)carbonyl, —$NR^4R^5$, —$SO_2NR^4R^5$, or —$CONR^4R^5$ where either $R^4$ are $R^5$ are each independently H or $C_1$-$C_4$ alkyl or $R^4$ and $R^5$ together with the nitrogen atom to which they are attached represent a saturated 5- or 6-membered heterocyclic group optionally containing a further heteroatom or group selected from O, S, NH, —$N(C_1$-$C_4$ alkyl) and —N.CHO; or (b) a bicyclic group which is an optionally substituted monocyclic 5- or 6- membered heterocycle as defined in (a) fused to an imidazole or benzene ring, said benzene ring being optionally substituted by $C_1$-$C_4$ alkyl, $C_1$-$C_4$ alkoxy or halo.

$R^3$ is most preferably a heterocyclic group selected from triazolyl, oxadiazolyl, pyrimidinyl or a partially saturated derivative thereof, purinyl, quinazolinyl, imidazolyl, imidazolinyl, triazinyl, pyridyl, thiazolyl, thiazolinyl, benzthiazolyl, thiadiazolyl, pyrazinyl, quinoxalinyl and pyrrolinyl, and their N- and S-oxides, $R^3$ being optionally substituted by $C_1$-$C_4$ alkyl, $C_1$-$C_4$ alkoxy, halo, hydroxy, oxo, cyano, 3-methylureido, phenyl, phenoxy, pyridyl, acetyl, carbamoyl, N-methylcarbamoyl, ($C_1$-$C_4$ alkoxy)carbonyl, —$NR^4R^5$, or —$SO_2NR^4R^5$, where either $R^4$ and $R^5$ are each independently H or $C_1$-$C_4$ alkyl or $R^4$ and $R^5$ together with the nitrogen atom to which they are attached form a piperidino, morpholino, 4-methylpiperazin-1-yl or 4-formylpiperazin-1-yl group.

1,2,4-Triazol-3-yl, 1,2,4-oxadiazol-3-yl, 1,2,5-thiadiazol-3-yl, pyrimidin-2-yl, pyrimidin-4-yl, imidazol-2-yl, 1,3,5-triazin-2-yl, pyrid-2-yl, thiazol-2-yl, pyrazin-2-yl and pyrrolin-2-yl, optionally substituted as above, represent typical instances of $R^3$.

The most preferred individual heterocyclic groups represented by $R^3$ are as follows:

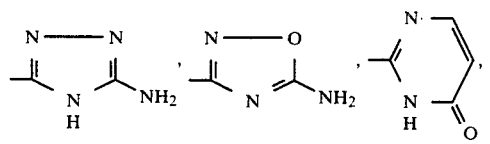

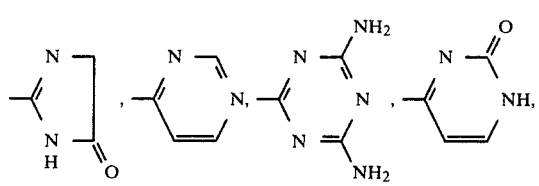

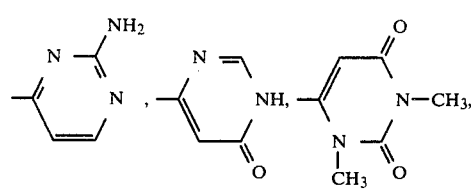

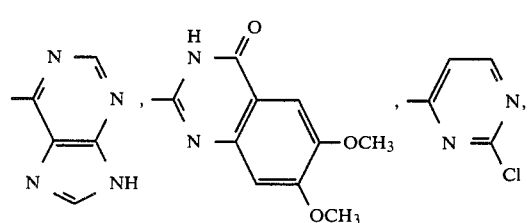

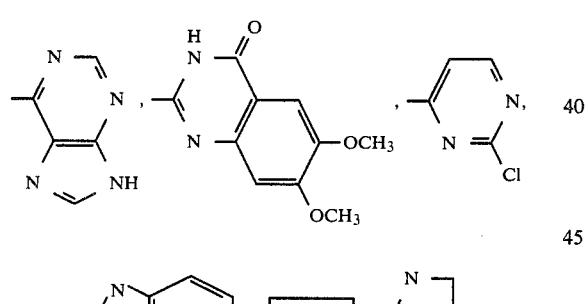

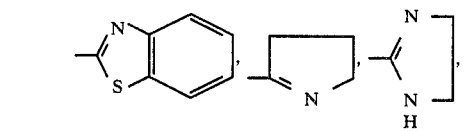

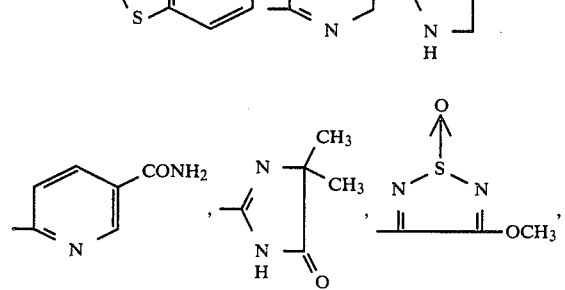

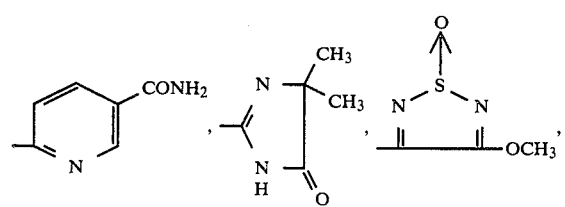

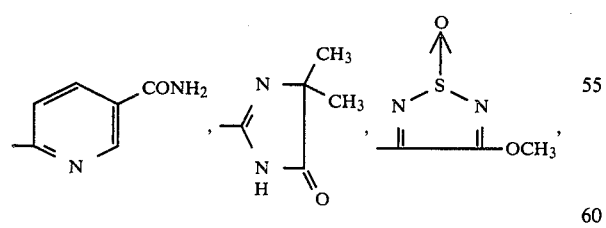

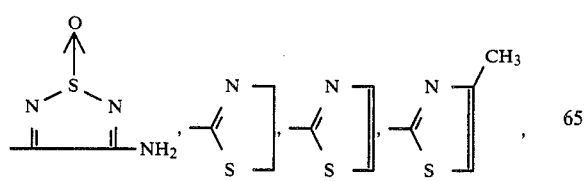

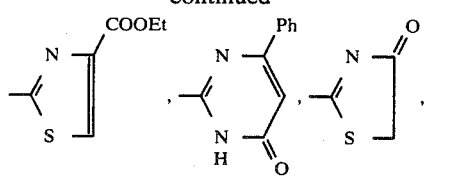

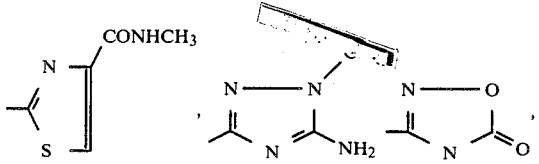

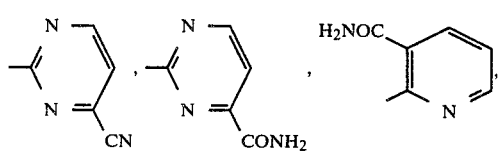

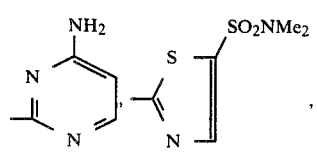

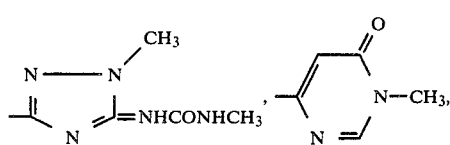

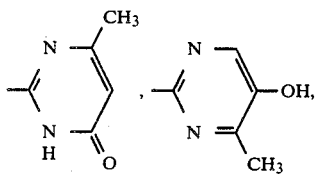

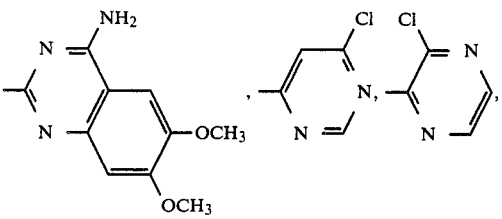

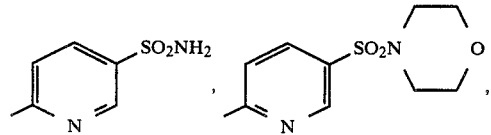

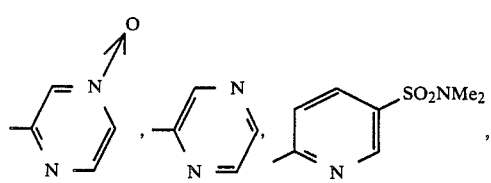

-continued

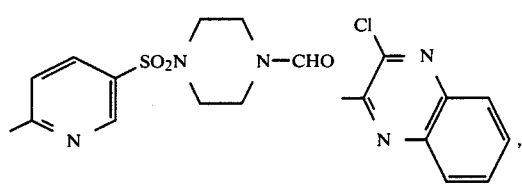

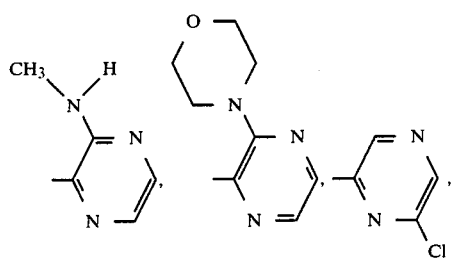

In some of these groups tautomerism may occur, e.g.

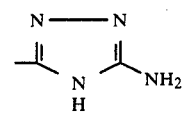

In such cases both tautomers are within the scope of this invention.

In the preferred individual compound, R is 2,3-dichlorophenyl, $R^1$ is $CH_3$, $R^2$ is $C_2H_5$, Y is $-(CH_2)_2-$ and $R^3$ is The compounds of the formula (I) containing one or more asymmetric centres will exist as one or more pairs of enantiomers, and such pairs or individual isomers may be separable by physical methods, e.g. by fractional crystallisation of the free bases or suitable salts or chromatography of the free bases. The invention includes the separated pairs as well as mixtures thereof, as racemic mixtures or as separated optically-active isomeric forms.

DETAILED DESCRIPTION OF THE INVENTION

The compounds of the invention can be prepared by a number of routes, including the following:

(1) The compounds of the formula (I) can be prepared via the following route:

Q is a facile leaving group, such as $-NH.NO_2$, $C_1-C_4$ alkylthio, $C_1-C_4$ alkoxy, Cl, Br or I. Q is preferably methylthio, methoxy, ethoxy, chloro or nitroamino.

The reaction is typically carried out by heating the reactants at 50°–130° C., e.g. under reflux, in a suitable organic solvent until the reaction is substantially complete. Typical organic solvents include methanol, ethanol, n-butanol, acetonitrile, dimethylformamide (DMF), methylene chloride, etc. When Q is $C_1-C_4$ alkylthio, Cl, Br or I, the presence of a base such as triethylamine, sodium carbonate or 4-dimethylaminopyridine is preferred. The product (I) can then be isolated and purified conventionally.

The starting materials of the formula (II) are the subject matter of our European patent application publication No. 0089167. Some typical methods for their preparation are however described in the Preparations hereinafter.

As disclosed in the said patent application, a typical route to the intermediates (II) is as follows:

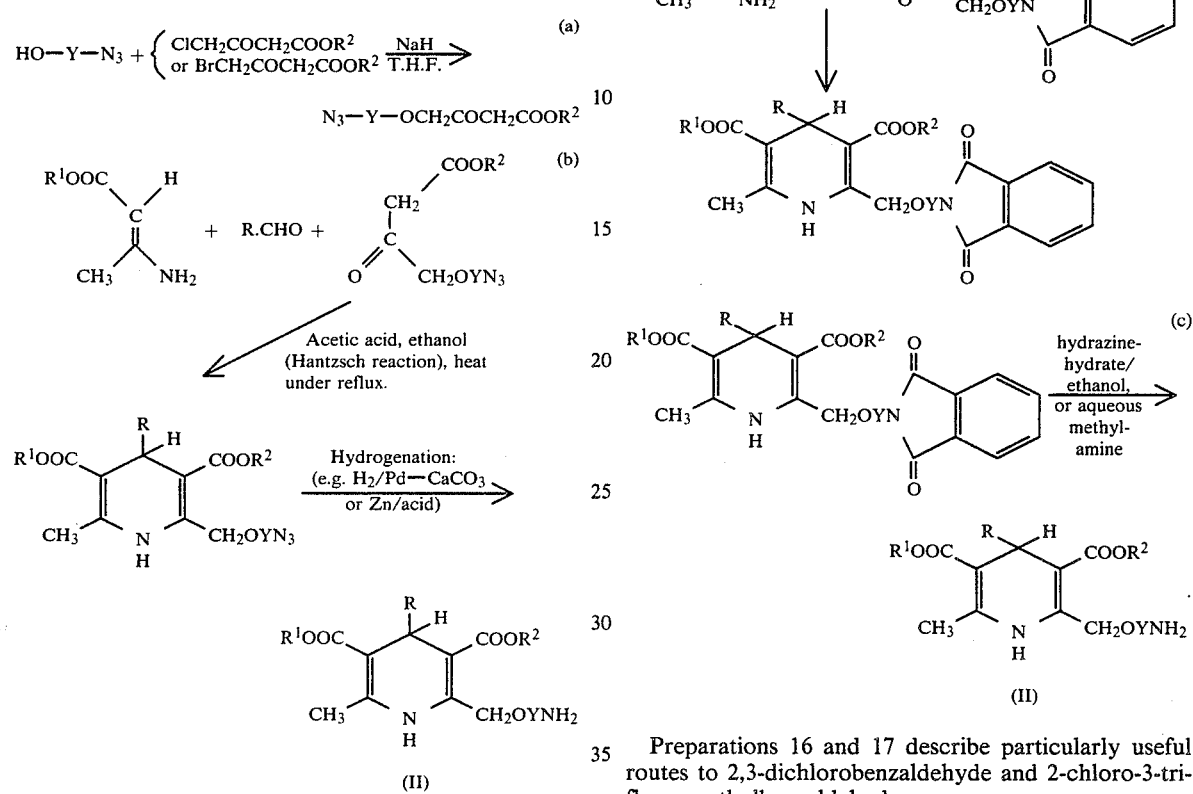

An alternative route to the intermediates (II) is as follows:

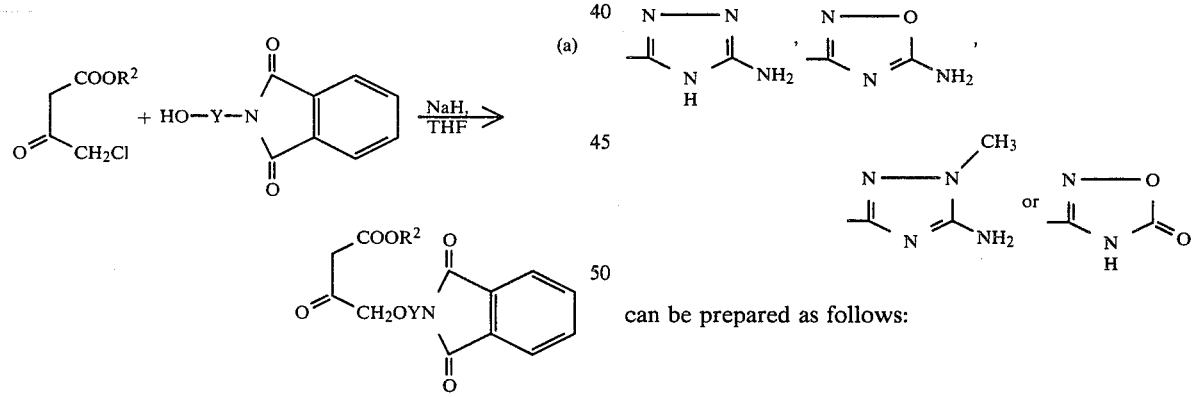

Preparations 16 and 17 describe particularly useful routes to 2,3-dichlorobenzaldehyde and 2-chloro-3-trifluoromethylbenzaldehyde.

(2) Compounds in which $R^3$ is can be prepared as follows:

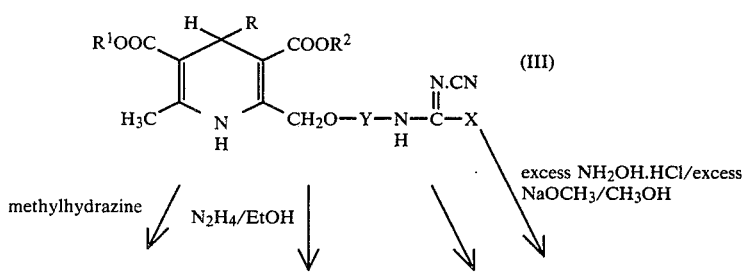

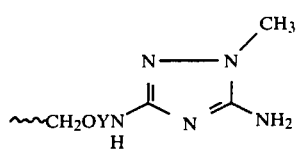
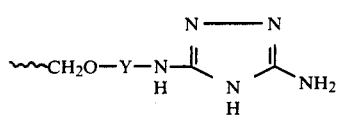
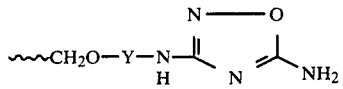
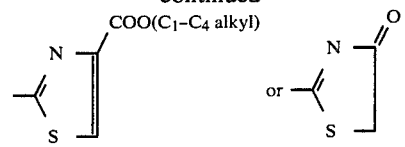

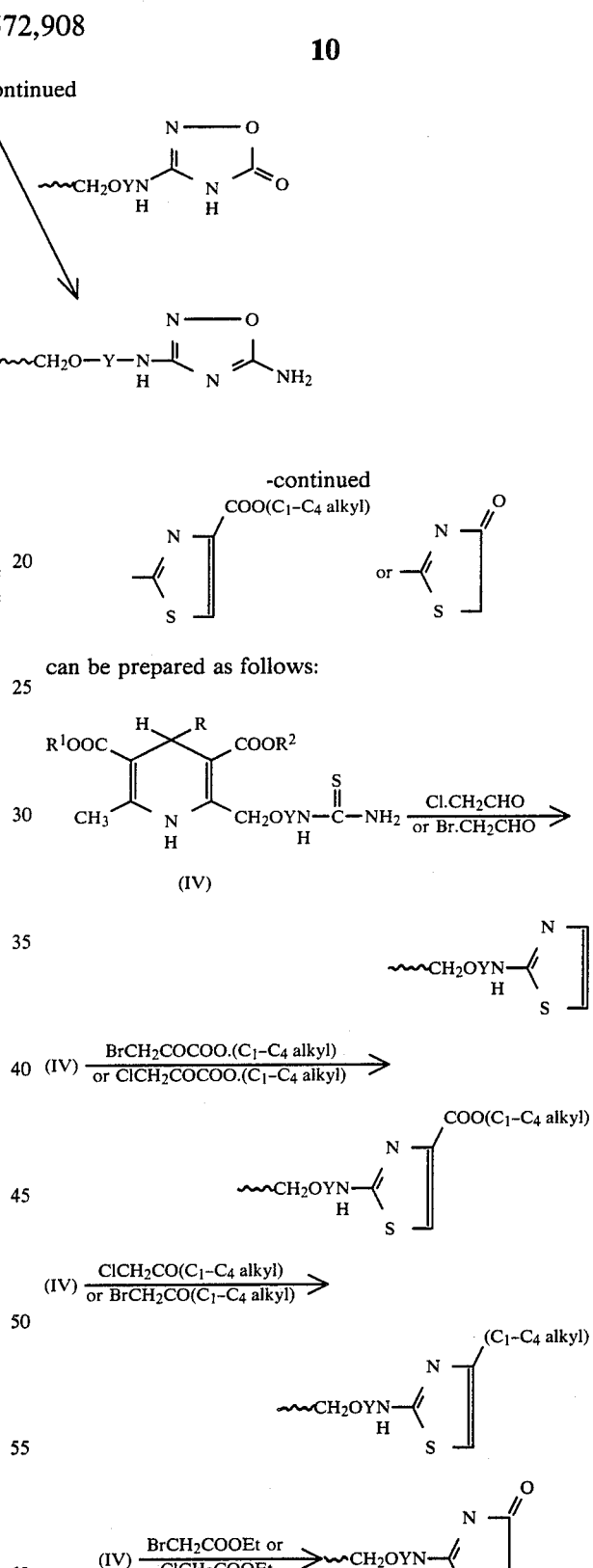

X is —SCH₃, —OCH₃ or —O.Phenyl.

These reactions are typically carried out in a suitable organic solvent such as methanol, ethanol, acetonitrile or tetrahydrofuran, with heating if necessary at up to 130° C. and preferably under reflux. Heating is preferred when ethanol is used as the solvent. The reaction is generally complete in about 4 hours. The desired product can then be isolated and purified conventionally.

The starting materials of the formula (III) can be prepared from compounds of the formula (II) [see route (1) above] as follows:

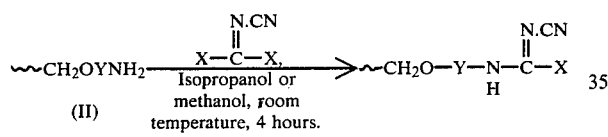

(3) Compounds in which R³ is

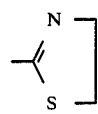

can be prepared from the compounds of the formula (II) as follows:

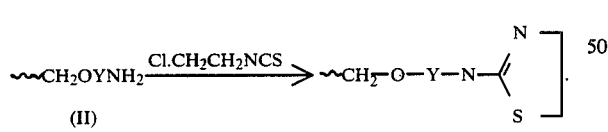

The reaction is typically carried out by stirring the reactants together in a suitable organic solvent, e.g. methylene chloride, for a few hours, and again the product can then be isolated and purified conventionally. The presence of base in the reaction mixture, e.g. triethylamine, is preferred.

(4) Compounds in which R³ is

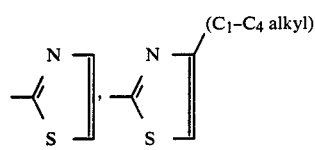

can be prepared as follows:

The reaction is typically carried out by stirring the reactants together at room temperature in a suitable solvent, e.g. CHCl₃/CH₃OH, until the reaction is substantially complete. If necessary, the reaction mixture can be heated to accelerate the reaction. The product can be isolated conventionally.

The starting materials of the formula (IV) can be prepared from the compounds of the formula (II) as follows:

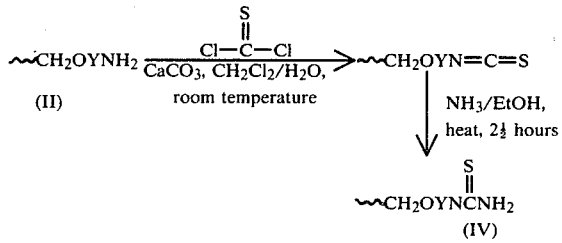

(5) Compounds in which $R^3$ is

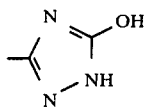

can be prepared as follows:

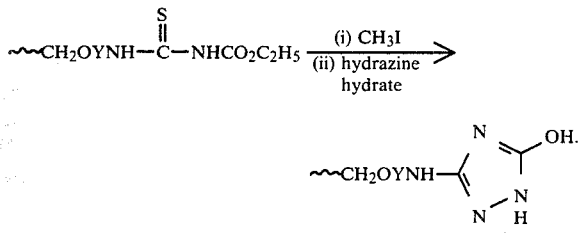

The starting ethoxycarbonylthioureido derivatives can be prepared as follows:

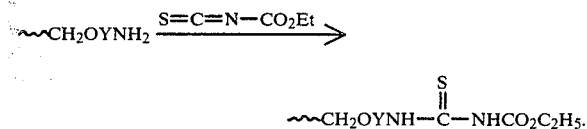

(6) Compounds in which $R^3$ is

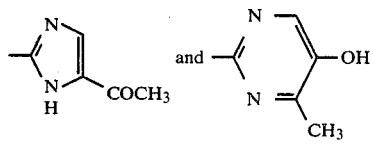

can be prepared by the reaction of the corresponding amino compound ($R^3$=H) with 5-acetyl-2-aminooxazole in aqueous methanol, typically by heating for 24 hours or so. The reaction produces a mixture of two products having $R^3$ as above. These can be separated by conventional chromatographic procedures.

(7) Some of the compounds of the formula (I) can be prepared from other compounds of the formula (I), e.g., those where $R^3$ is a heterocyclic group substituted by an [$C_1$-$C_4$-alkyl]carbamoyl group can be prepared by the reaction of the corresponding compounds in which the heterocyclic group is substituted by ($C_1$-$C_4$ alkoxy)carbonyl with a $C_1$-$C_4$ alkylamine. Similarly, compounds in which $R^3$ is substituted by —$NH_2$ can be prepared by reacting the corresponding methoxy-substituted derivatives with ammonia, generally in ethanol, and compounds in which $R^3$ is substituted by —NHCONH(-$C_1$-$C_4$ alkyl) by reaction of the corresponding amino-substituted compound with a $C_1$-$C_4$ alkylisocyanate.

Compounds in which $R^3$ is a heterocyclic group substituted by an amino or substituted amino group, or a cyclic amino group, e.g. morpholino, piperidino or N-methyl piperazino, can be prepared by heating the corresponding chloro-substituted compound with the appropriate amine.

Compounds in which $R^3$ is pyrazinyl can be prepared by the reduction of the corresponding compound in which $R^3$ is a pyrazine-N-oxide with sodium dithionate, e.g. by heating in aqueous ethanol.

(8) Acid addition salts can be prepared conventionally, e.g. by reacting a solution of the free base in a suitable organic solvent with a solution of the desired acid in a suitable solvent, and either recovering the salt by filtration when it precipitates from solution, or by evaporation of the solution to dryness.

The ability of the compounds to inhibit the movement of calcium into the cell is shown by their effectiveness in reducing the response of isolated heart tissue to an increase in calcium ion concentration in vitro. The test is performed by mounting spirally cut strips of rat aorta with one end fixed and the other attached to a force transducer. The tissue is immersed in a bath of physiological saline solution containing potassium ions at a concentration of 45 millimolar and no calcium. Calcium chloride is added to the bath with a pipette to give a final calcium ion concentration of 2 millimolar. The change in tension caused by the resulting contraction of the tissue is noted. The bath is drained and replaced with fresh saline solution and, after 45 minutes, the test is repeated with the particular compound under test present in the saline solution. The concentration of compound required to reduce the response by 50% ($IC_{50}$) is recorded.

The antihypertensive activity of the compounds is also evaluated after oral administration by measuring the fall in blood pressure in spontaneously hypertensive rats or renally hypertensive dogs.

For administration to man in the curative or prophylactic treatment of cardiac conditions and hypertension, oral dosages of the compounds will be in the range of from 5-100 mg daily for an average adult patient (70 kg), typically 10-60 mg daily. Thus for a typical adult patient, individual tablets or capsules will generally contain from 5, 10 or 20 mg of active compound, in a suitable pharmaceutically acceptable vehicle or carrier. Dosages for intravenous administration will typically be within the range 1 to 10 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosages ranges are merited, and such are within the scope of this invention.

For human use, the compounds of the formula (I) can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic.

Thus in a further aspect the invention provides a pharmaceutical composition comprising a compound of the formula (I), or a pharmaceutically acceptable acid addition salt thereof, together with a pharmaceutically acceptable diluent or carrier.

The invention also includes a compound of the formula (I), or a pharmaceutically acceptable acid addition salt thereof, for use in medicine, in particular in the treatment of ischaemic heart disease, angina, or hypertension in a human being.

The invention also provides a method of protecting the heart from the deleterious effects of ischaemia, which comprises administering an effective amount of a compound of the formula (I) or pharmaceutically acceptable acid addition salt thereof, or pharmaceutical composition as defined above.

The invention also includes a method of treating hypertension which comprises administering an antihypertensive amount of a compound of the formula (I) or pharmaceutically acceptable acid addition salt thereof, or pharmaceutical composition as defined above.

The following Examples illustrate the invention. All temperatures are in °C.:

EXAMPLE 1

A.
N-{2-[(4-{2-Chlorophenyl}-3-ethoxycarbonyl-5-methoxycarbonyl-6-methyl-1,4-dihydropyrid-2-yl)methoxy]ethyl}-N'-cyano-S-methyl-isothiourea

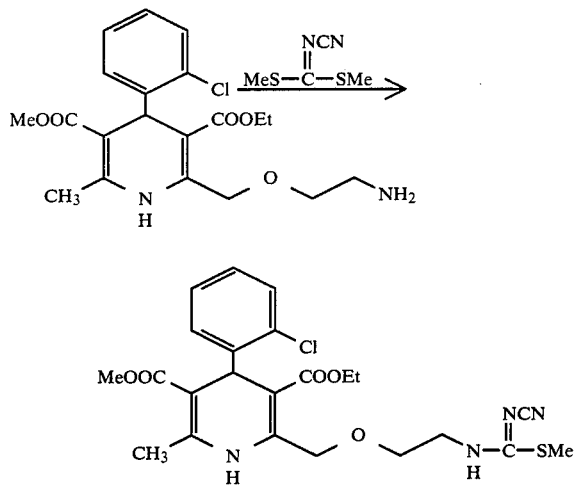

2-[2-Aminoethoxymethyl]-3-ethoxycarbonyl-4-(2-chlorophenyl)-5-methoxycarbonyl-6-methyl-1,4-dihydropyridine (4.3 g) and dimethyl N-cyanoimidodithiocarbonate (2 g) in isopropanol (15 ml) were allowed to stand at room temperature for 4 hours. Ether (30 ml) was then added and the mixture was stood at room temperature overnight. The crystalline precipitate was filtered, washed with ether and dried, yield of the title compound 5.0 g, m.p. 177°–179°.

Analysis %: Found: C, 54.35; H, 5.4; N, 11.2. Calculated for $C_{23}H_{27}ClN_4O_5S$: C, 54.5; H, 5.4; N, 11.05.

B.
2-[2-(3-Amino-1H-1,2,4-triazol-5-ylamino)ethoxymethyl]-4-(2-chlorophenyl)-3-ethoxycarbonyl-5-methoxycarbonyl-6-methyl-1,4-dihydropyridine

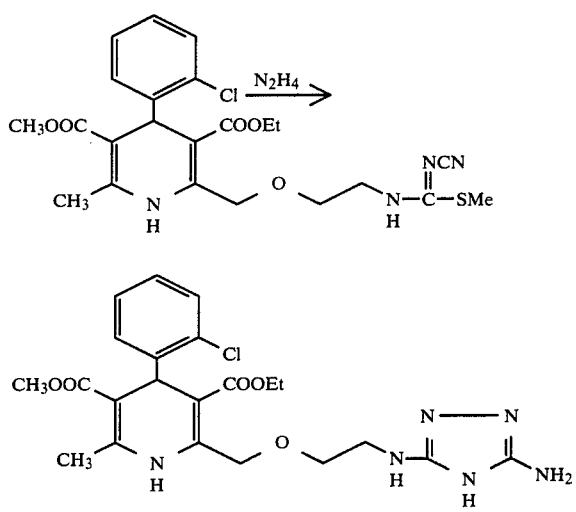

N-{2-[(4{-2-Chlorophenyl}-3-ethoxycarbonyl-5-methoxycarbonyl-6-methyl-1,4-dihydropyrid-2-yl)methoxy]ethyl}-N'-cyano-S-methyl-isothiourea (0.4 g) and hydrazine hydrate (0.15 ml) were dissolved in ethanol (20 ml) and heated under reflux for 3 hours. The solvent was then evaporated and toluene (10 ml) was added to the residue, and again the solution was evaporated to dryness. The residue was chromatographed on Merck "Kieselgel 60H" (Trade Mark), eluting with 2% methanol in methylene chloride, to give a beige solid. The solid was recrystallized from ethyl acetate plus a trace of ether to give the title compound, yield 0.1 g, m.p. 137°–138°.

Analysis %: Found: C, 53.45; H, 5.5; N, 17.2. Calculated for $C_{22}H_{27}ClN_6O_5$: C, 53.8; H, 5.55; N, 17.1.

Part (A) was repeated using $(MeO)_2C=N.CN$ in place of $(MeS)_2C=N.CN$ and using the same reaction conditions. The resulting intermediate had —OMe in place of —SMe, and this intermediate was converted by the method of part (B), i.e. using hydrazine hydrate, to the title compound of part (B).

EXAMPLE 2

2-[2-(3-Amino-1H-1,2,4-triazol-5-ylamino)ethoxymethyl]-4-(2-chloro-3-trifluoromethylphenyl)-3-ethoxycarbonyl-5-methoxycarbonyl-6-methyl-1,4-dihydropyridine

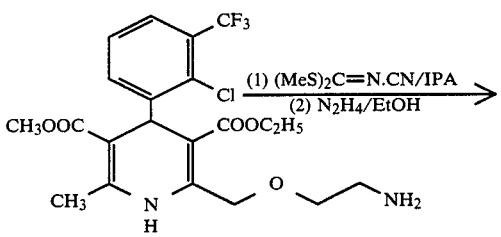

15
-continued

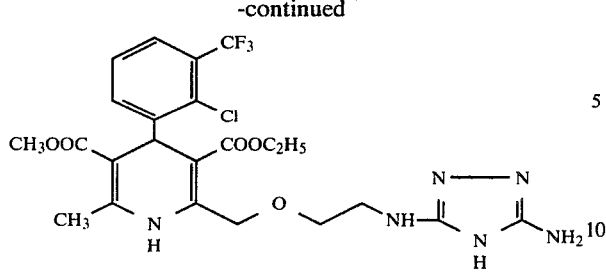

2-(2-Aminoethoxymethyl)-4-(2-chloro-3-trifluoromethylphenyl)-3-ethoxycarbonyl-5-methoxycarbonyl-6-methyl-1,4-dihydropyridine (0.5 g) and dimethyl N-cyanoimidodithiocarbonate (0.16 g) in isopropanol (5 ml) were stirred together at room temperature for 4 hours. Ether (10 ml) was then added and the mixture was stirred for a further 2 hours. The precipitated isothiourea was filtered, washed with dry ether, dried and used directly without further purification. The solid was dissolved in ethanol (10 ml) and heated to reflux while hydrazine hydrate (0.2 ml) was added in three portions. After 3 hours at reflux, the solution was evaporated to dryness and the residue was crystallised from ethyl acetate to give the title compound, m.p. 144°–145°.

Analysis %: Found: C, 49.4; H, 4.7; N, 15.0. Calculated for $C_{23}H_{26}ClF_3N_6O_5$: C, 49.6; H, 4.7; N, 15.0.

EXAMPLE 3

A. The following compound, m.p. 215°–217°, was prepared similarly to Example 1A, but starting from the corresponding 4-(2,3-dichlorophenyl)-1,4-dihydropyridyl derivative:

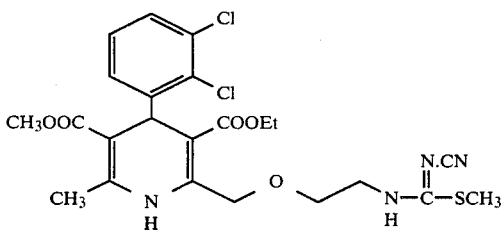

Analysis %: Found: C, 50.7; H, 5.05; N, 10.1. Calculated for $C_{23}H_{26}Cl_2N_4O_5S$: C, 51.02; H, 4.85; N, 10.35.

B. This compound was then reacted with hydrazine hydrate according to the procedure of Example 1B to produce the following product, m.p. 195°–6°:

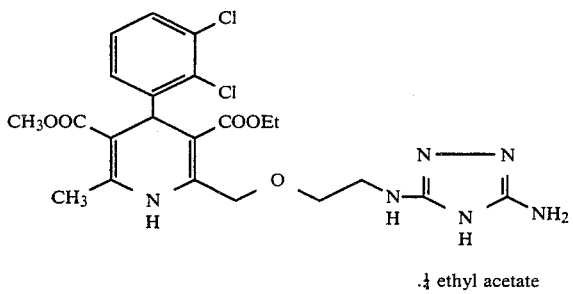

.¼ ethyl acetate

16
Analysis %: Found: C, 50.2; H, 5.35; N, 15.6. Calculated for $C_{22}H_{26}Cl_2N_6O_5.\frac{1}{4}C_4H_8O_2$: C, 50.45; H, 5.15; N, 15.35.

EXAMPLE 4

The following compound, m.p. 110°–111°, was prepared similarly to Example 1B, but using methyl hydrazine:

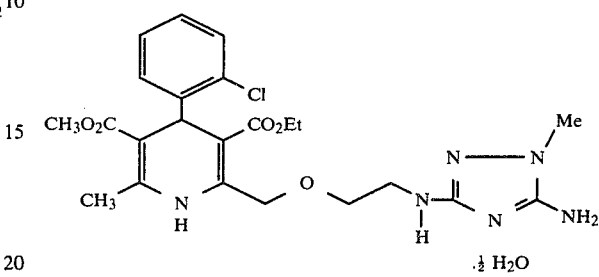

.½ H₂O

Analysis %: Found: C, 54.1; H, 5.8; N, 16.3. Calculated for $C_{23}H_{29}ClN_6O_5.\frac{1}{2}H_2O$: C, 53.7; H, 5.9; 16.35.

EXAMPLE 5

The following compound m.p. 118°–120.5° was prepared similarly to Example 3B, but using methyl hydrazine:

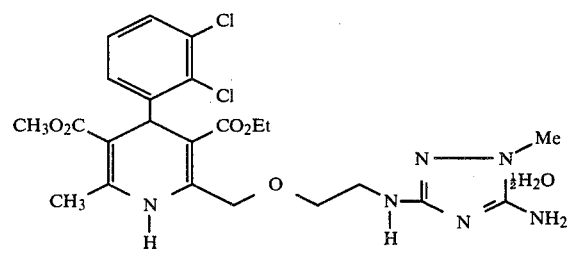

Analysis %: Found: C, 50.6; H, 5.3; N, 15.0. Calculated for $C_{23}H_{28}Cl_2N_6O_5.\frac{1}{2}H_2O$: C, 50.4; H, 5.3; N, 15.3.

EXAMPLE 6

2-[2-(5-Amino-1,2,4-oxadiazol-3-ylamino)ethoxymethyl]-4-(2-chlorophenyl)-3-ethoxycarbonyl-5-methoxycarbonyl-6-methyl-1,4-dihydropyridine

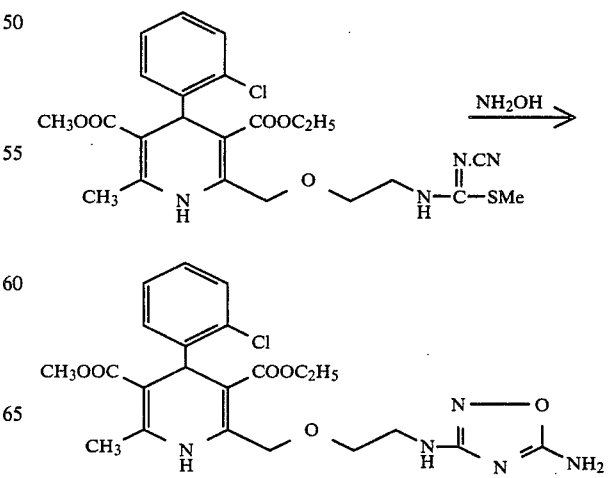

The N'-cyano-S-methyl-isothiourea from Example 1A (0.4 g) and hydroxylamine (0.2 g) in methanol (20 ml) were heated under reflux for 3 hours. The solvent was then evaporated, and the residue was chromatographed on "Kieselgel 60H" (Trade Mark), eluting with chloroform to give a solid which was recrystallised from 1:1 toluene/ether to give the title compound, yield 0.29 g, m.p. 135°.

Analysis %: Found: C, 53.8; H, 5.4; N, 14.25. Calculated for $C_{22}H_{26}ClN_5O_6$: C, 53.7; H, 5.3; N, 14.25.

EXAMPLE 7

The following compound, m.p. 114°, was prepared similarly to the procedure of Example 6 but using the corresponding 2-chloro-3-trifluoromethyl isothiourea intermediate as prepared in Example 2:

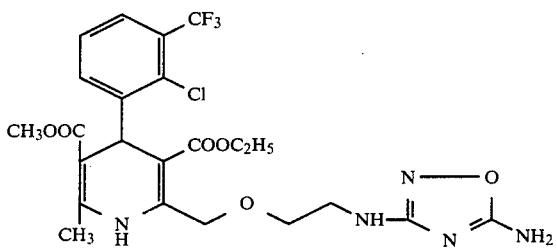

Analysis %: Found: C, 49.6; H, 4.7; N, 12.4. Calculated for $C_{23}H_{25}ClF_3N_5O_6$: C, 49.3; H, 4.5; N, 12.5.

EXAMPLE 8

4-(2-Chlorophenyl)-3-ethoxycarbonyl-5-methoxycarbonyl-6-methyl-2-[2-(3,4-dihydro-4-oxo-pyrimidin-2-ylamino)ethoxymethyl]-1,4-dihydropyridine

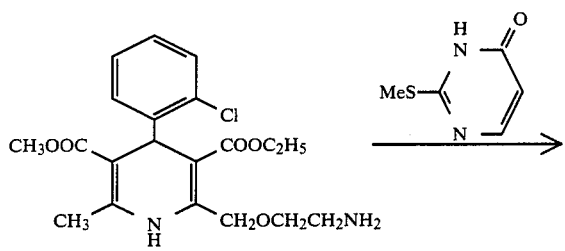

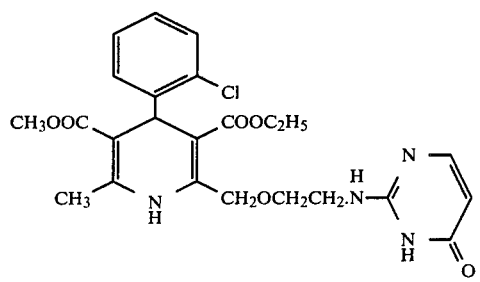

2-[2-Aminoethoxymethyl]-3-ethoxycarbonyl-4-(2-chlorophenyl)-5-methoxycarbonyl-6-methyl-1,4-dihydropyridine (0.75 g) and 2-methylthio-3H-pyrimid-4-one (0.5 g) were dissolved in ethanol (5 ml) and heated under reflux for 20 hours. The solvent was evaporated and the residue was partitioned between ethyl acetate and water. The organic layer was separated, washed with 2N hydrochloric acid to remove any unreacted amine, and then with dilute sodium hydroxide solution. It was then washed with water, dried, filtered and evaporated to give a yellow gum. Chromatography on silica "Kieselgel 60H" (Trade Mark) eluting with ethyl acetate gave the title compound, which was recrystallised from ethyl acetate, yield 171 mg, m.p. 148°–150°.

Analysis %: Found: C, 57.3; H, 5.55; N, 11.4. Calculated for $C_{24}H_{27}ClN_4O_6$: C, 57.3; H, 5.4; N, 11.15.

EXAMPLES 9–36

The following compounds were prepared similarly to the previous Example, i.e., by the following reaction:

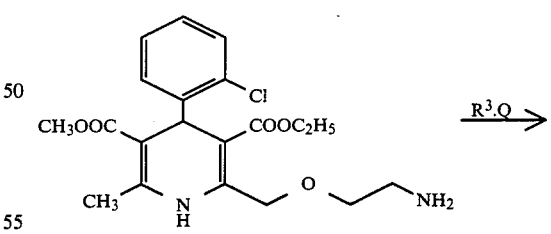

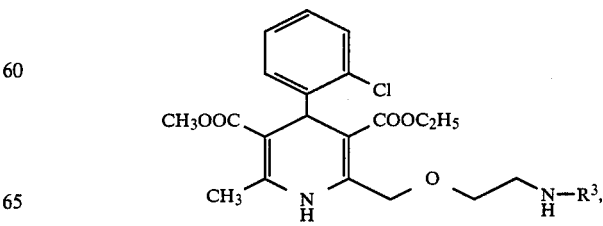

and were characterised in the form indicated:

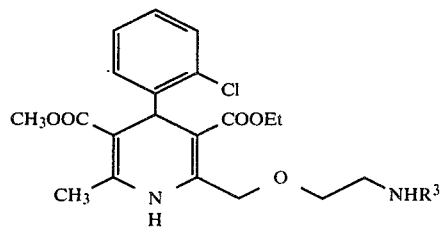

| Example No. | R³ | Q | Reaction Solvent | Base | Reaction Time | Form Isolated | m.p. (°C.) | Analysis % (Theoretical in brackets) C | H | N |
|---|---|---|---|---|---|---|---|---|---|---|
| 9 | (imidazolyl-CH₂-C(=O)-, NH) | MeS— | EtOH | Et₃N | 4 hrs. | Free base | 155–157 | 55.8 (56.25 | 5.55 5.55 | 11.3 11.4) |
| 10 | (pyrimidinyl) | Cl | CH₃CN | Na₂CO₃ | 6 hrs. | Free base | 137 | 59.05 (59.2 | 5.7 5.6 | 11.3 11.5) |
| 11 | (diamino-triazinyl) | Cl | MeOH | Et₃N | 12 hrs. | Free base | 186–189 | 53.25 (53.3 | 5.5 5.45 | 18.6 18.9) |
| 12 | (oxo-pyrimidinyl, NH) | Cl | n-BuOH | Et₃N | 60 hrs. | Free base | 225 | 56.5 (57.35 | 5.4 5.4 | 11.05 11.15) |
| 13 | (amino-pyrimidinyl) | Cl | n-BuOH | Et₃N | 60 hrs. | Free base | 172–174 | 57.2 (57.4 | 5.8 5.6 | 13.8 13.95) |
| 14 | (oxo-pyrimidinyl) | Cl | n-BuOH | Et₃N | 18 hrs. | Free base | 120–122 | 56.9 (57.35 | 5.3 5.4 | 10.9 11.15) |
| 15 | (N,N-dimethyl dioxo-pyrimidinyl) | Cl | n-BuOH | Et₃N | 18 hrs. | Free base, H₂O | 122 | 55.2 (55.25 | 5.85 5.9 | 9.8 9.9) |
| 16 | (purinyl) | Cl | CH₃CN | Na₂CO₃ | 5 hrs. | Free base | 153–155 | 56.9 (57.0 | 5.15 5.2 | 15.9 15.95) |

-continued

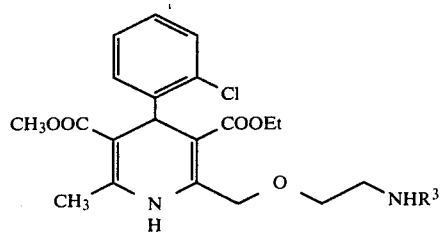

| Example No. | R³ | Q | Reaction Solvent | Base | Reaction Time | Form Isolated | m.p. (°C.) | Analysis % (Theoretical in brackets) C | H | N |
|---|---|---|---|---|---|---|---|---|---|---|
| 17 | 2-(3,4-dimethoxyphenyl)-NHC(O)- pyrimidinyl group (H-N=C with methyl, attached to 3,4-dimethoxybenzamide) | Cl | n-BuOH | Et₃N | 20 hrs. | Free base | 205–207 | 57.35 (58.8 | 5.3 5.4 | 8.9 9.15) |
| 18 | 2-chloropyrimidin-4-yl | Cl | MeOH | Et₃N | 2 hrs. | Free base | 160 | 55.35 (55.3 | 5.2 5.0 | 10.9 10.75) |
| 19 | benzothiazol-2-yl | Cl | D.M.F. | Na₂CO₃ | 5 hrs. | Free base | 176–177 | 59.75 (59.8 | 5.4 5.2 | 7.55 7.75) |
| 20 | 4,5-dihydro-2H-pyrrol-2-yl (imino) | —OEt | EtOH | — | 3½ hrs. | Hydro-chloride | 166–167 | 56.2 (56.25 | 6.15 6.1 | 8.35 8.2) |
| 21 | imidazolin-2-yl | —SMe | EtOH | Et₃N | 6 hrs. | Acetate | 164 | 55.05 (55.9 | 6.15 6.2 | 10.45 10.45) |
| 22 | 6-methyl-5-carbamoylpyridin-2-yl | Cl | n-BuOH | 4-dimethyl-amino-pyridine | 18 hrs. | Maleate 2.H₂O | 156–158 | 53.9 (53.85 | 5.1 5.0 | 8.4 8.3) |
| 23 | 4,4-dimethyl-5-oxo-imidazolin-2-yl | —SMe | EtOH | Et₃N | 1 hr. | Free base | 226–228 | 57.5 (57.8 | 6.0 6.0 | 10.8 10.8) |
| 24 | 4-methyl-5-oxo-imidazolin-2-yl | —NHNO₂ | n-BuOH | — | 18 hrs. | Hemi-fumarate | 197–199(d) | 56.3 (56.4 | 5.4 5.4 | 9.8 9.7) |

-continued

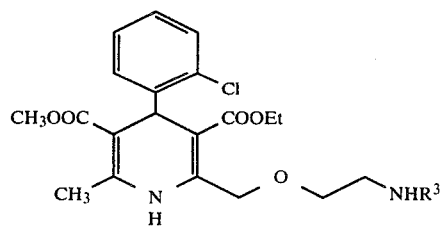

| Example No. | R³ | Q | Reaction Solvent | Base | Reaction Time | Form Isolated | m.p. (°C.) | Analysis % (Theoretical in brackets) C | H | N |
|---|---|---|---|---|---|---|---|---|---|---|
| 25 | 2-methyl-3-carbamoyl-pyridinyl (CONH₂) | —Cl | n-BuOH | 4-dimethyl-amino-pyridine | 18 hrs. | Maleate | 163.5–164 | 56.0 (56.1 | 5.1 4.7 | 8.6 8.7) |
| 26 | 2-methyl-thiazol-5-yl with SO₂N(CH₃)₂ | —Cl | n-BuOH | 4-dimethyl-amino-pyridine | 24 hrs. | Free base | 125 | 50.1 (50.1 | 5.1 5.2 | 9.1 9.3) |
| 27 | 4-amino-pyrimidin-2-yl (NH₂) | Cl | n-BuOH | Et₃N | 60 hrs. | Free base Hemi-etherate | 101–104 | 57.7 (57.9 | 6.2 6.2 | 12.9 13.0) |
| 28 | 4-cyano-pyrimidin-2-yl (CN) | —Cl | n-BuOH | 4-dimethyl-amino-pyridine | 20 hrs. | Free base | 133–134 | 58.4 (58.7 | 5.2 5.1 | 13.3 13.7) |
| 29 | 4-carbamoyl-pyrimidin-2-yl (CONH₂) | —Cl | n-BuOH | 4-dimethyl-amino-pyridine | 4 hrs. | Free base | 211 | 56.5 (56.7 | 5.3 5.3 | 13.0 13.2) |
| 30 | 1-methyl-2-oxo-pyridinyl (N—CH₃) | —Cl | n-BuOH | 4-dimethyl-amino-pyridine | 18 hrs. | ½.Ethyl acetate | 124–126 | 57.4 (57.8 | 5.8 5.6 | 10.0 10.0) |
| 31 | 4-chloro-pyrimidin-2-yl (Cl) | Cl | CH₂Cl₂ | Et₃N | 26 hours | Free base | 115 | 55.1 (55.3 | 5.1 5.0 | 10.6 10.75) |
| 32 | 3-chloro-pyrazin-2-yl (Cl) | Cl | EtOH | Et₃N | 18 hours | Free base | 110 | 55.4 (55.3 | 5.35 5.0 | 10.4 10.75) |

-continued

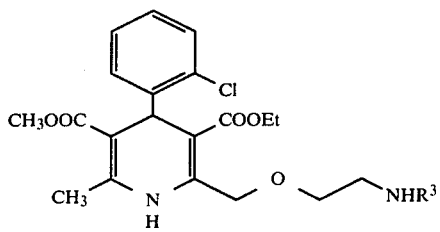

| Example No. | R³ | Q | Reaction Solvent | Base | Reaction Time | Form Isolated | m.p. (°C.) | Analysis % (Theoretical in brackets) C | H | N |
|---|---|---|---|---|---|---|---|---|---|---|
| 33 | (pyrazinyl-Cl) | Cl | EtOH | Et₃N | 18 hours | Free base | 142–144 | 55.3 (55.3 | 4.9 5.0 | 10.6 10.75) |
| 34 | (4-amino-6,7-dimethoxy-2-methylquinazoline) | Cl | BuOH | 4-Dimethyl-amino pyridine | 18 hours | Free base | 172–173 | 58.4 (58.9 | 5.8 5.6 | 11.5 11.4) |
| 35 | (6-methylpyridin-3-yl-SO₂NH₂) | Cl | BuOH | Et₃N | 48 hours | Free base | 165–168 | 53.5 (53.1 | 5.25 5.2 | 9.8 9.9) |
| 36 | (6-methylpyridin-3-yl-SO₂N(piperazinyl)N—CHO) | Cl | EtOH | Et₃N | 60 hours | Hemi-hydrate | 165–167 | 53.9 (53.8 | 5.5 5.6 | 10.75 10.45) |

EXAMPLES 37–57

The following compounds were prepared similarly to Example 8, i.e. by the following reaction:

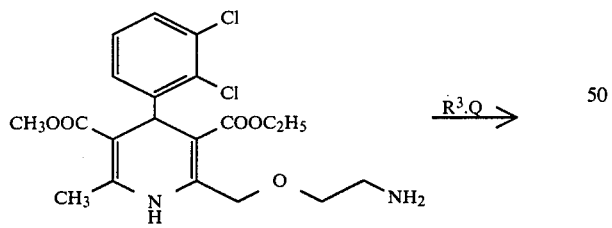 $\xrightarrow{R^3Q}$ 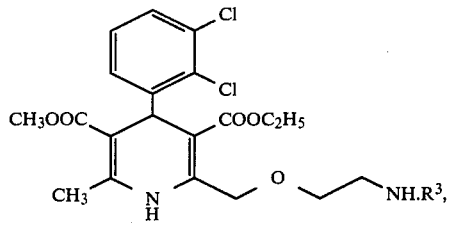

and were characterised in the form indicated:

| Example No | R³ | Q | Reaction Solvent | Base | Reaction Time | Form Isolated | m.p. (°C.) | Analysis % (Theoretical in brackets) C | H | N |
|---|---|---|---|---|---|---|---|---|---|---|
| 37 | (2-methylimidazolin-4-one) | —SMe | EtOH | Et₃N | 3 hrs. | Hemihydrate | 218 (d) | 51.7 (51.7 | 5.0 5.1 | 10.3 10.5) |

-continued

| Example No | R³ | Q | Reaction Solvent | Base | Reaction Time | Form Isolated | m.p. (°C.) | Analysis % (Theoretical in brackets) C | H | N |
|---|---|---|---|---|---|---|---|---|---|---|
| 38 | 2-methyl-5,5-dimethyl-6-oxo-1,6-dihydropyrimidin-4-yl | —SMe | EtOH | Et₃N | 22 hrs. | Free base | 225–227 | 53.2 (53.4 | 5.4 5.6 | 10.0 10.0) |
| 39 | 2-methyl-6-oxo-1,6-dihydropyrimidin-4-yl | —SMe | EtOH | Et₃N | 24 hrs. | Hemihydrate | 142–145 | 52.5 (52.7 | 4.7 5.0 | 10.4 10.3) |
| 40 | 2-amino-pyrimidin-4-yl | —Cl | n-BuOH | Et₃N | 36 hrs. | Free base | 179 | 53.5 (53.7 | 5.2 5.1 | 13.0 13.1) |
| 41 | 6-oxo-1,6-dihydropyrimidin-4-yl | —Cl | n-BuOH | 4-dimethyl-amino-pyridine | 30 hrs. | Free base hemi-hydrate | 132–134 | 52.9 (52.75 | 4.8 5.0 | 10.5 10.3) |
| 42 | 2,5-dimethyl-6-oxo-1,6-dihydropyrimidin-4-yl | —NHNO₂ | n-BuOH | — | 18 hrs. | Fumarate | 144–146 | 52.4 (52.2 | 4.9 4.8 | 8.6 8.4) |
| 43 | 2-methyl-6-oxo-5-phenyl-1,6-dihydropyrimidin-4-yl | —NHNO₂ | BuOH | — | 18 hours | Free base | 201 | 56.3 (56.0 | 4.7 4.8 | 7.7 8.1) |
| 44 | 2-methyl-6-oxo-5-(pyridin-2-yl)-1,6-dihydropyrimidin-4-yl | —NHNO₂ | BuOH | — | 18 hours | Free base | 205–206 | 56.65 (56.7 | 4.9 4.8 | 11.0 11.4) |
| 45 | 6-methyl-5-(morpholin-4-ylsulfonyl)pyridin-2-yl | Cl | BuOH | Et₃N | 18 hours. | Free base | 177.5–178.5 | 51.7 (52.0 | 5.1 5.1 | 8.5 8.4) |

| Example No | R³ | Q | Reaction Solvent | Base | Reaction Time | Form Isolated | m.p. (°C.) | Analysis % (Theoretical in brackets) C | H | N |
|---|---|---|---|---|---|---|---|---|---|---|
| 46 | 6-methyl-pyridin-3-yl-SO₂N(piperidine) | Cl | BuOH | 4-Dimethyl amino pyridine | 32 hours | Sesqui-hydrate | 182–183.5 | 51.7 (51.9 | 5.3 5.7 | 7.9 8.1) |
| 47 | 6-methyl-pyridin-3-yl-SO₂NMe₂ | Cl | EtOH | Et₃N | 66 hours | Free base | 101–104 | 51.55 (51.7 | 5.3 5.1 | 9.0 9.0) |
| 48 | 4-amino-2-methyl-6,7-dimethoxyquinazoline | Cl | BuOH | 4-Dimethyl amino pyridine | 18 hours | Free base | 190 | 55.6 (55.7 | 5.2 5.15 | 10.6 10.8) |
| 49 | 3-chloro-2-methylquinoxaline | Cl | EtOH | Et₃N | 18 hours | Free base | 101–103 | 55.2 (55.5 | 4.6 5.0 | 9.00 9.25) |
| 50 | 5-methylpyrazine 1-oxide | Cl | EtOH | Et₃N | 17 hours | Free base | 148–150 | 53.5 (53.6 | 5.0 4.9 | 10.4 10.4) |
| 51 | 3-chloro-2-methylpyrazine | Cl | EtOH | Et₃N | 18 hours | Free base | 111–112 | 51.6 (51.9 | 4.3 4.5 | 10.2 10.1) |
| 52 | 3-chloro-6-methylpyrazine | Cl | EtOH | Et₃N | 18 hours | Free base | 113–115 | 51.8 (51.9 | 4.6 4.5 | 10.0 10.1) |
| 53 | 4-chloro-6-methylpyrimidine | Cl | EtOH | Et₃N | 4 hours | Free base | 110 | 51.7 (51.9 | 4.5 4.5 | 9.9 10.1) |
| 54 | 4-methoxy-6-methylpyrimidine | Cl | BuOH | Et₃N | 48 hours | Free base | 162–164 | 56.8 (57.0 | 4.8 5.3 | 9.2 9.2) |
| 55 | 4-phenoxy-6-methylpyrimidine | Cl | BuOH | Et₃N | 10 hours | Free base | 146–148 | 58.4 (58.7 | 5.0 4.9 | 9.3 9.1) |
| 56 | 2-methylpyrimidine | Cl | BuOH | Et₃N | 7 hours | Free base | 158–160 | 55.5 (55.3 | 5.0 5.0 | 10.9 10.75) |

-continued

| Example No | R³ | Q | Reaction Solvent | Base | Reaction Time | Form Isolated | m.p. (°C.) | Analysis % (Theoretical in brackets) C | H | N |
|---|---|---|---|---|---|---|---|---|---|---|
| 57 | (pyrimidine with OiPr) | Cl | BuOH | Et₃N | 17 hours | Free base | 137–139 | 55.8 (56.0 | 5.7 5.6 | 9.8 9.7) |

EXAMPLES 58–63

The following compounds were prepared similarly to Example 8, i.e. by the following reaction:

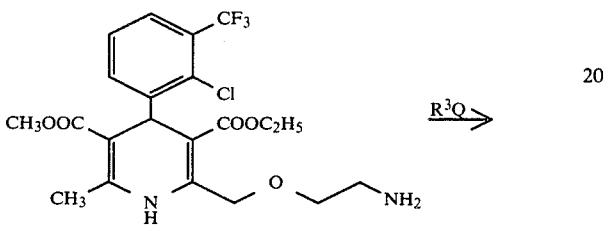 $\xrightarrow{R^3Q}$

-continued

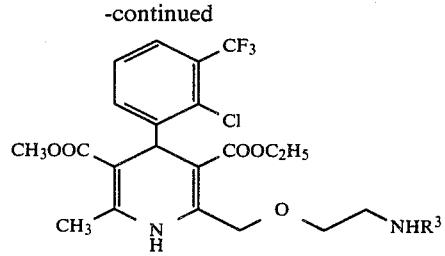

and were characterised in the form indicated:

| Example No. | R³ | Q | Reaction Solvent | Base | Reaction Time | Form Isolated | m.p. (°C.) | Analysis % (Theoretical in brackets) C | H | N |
|---|---|---|---|---|---|---|---|---|---|---|
| 58 | (2-methyl-imidazolin-4-one) | —SMe | EtOH | Et₃N | 4 hours | Hemihydrate | 206–208 | 50.4 (50.75 | 4.7 4.8 | 9.7 9.9) |
| 59 | (2-methylpyrimidinone) | —SMe | EtOH | — | 24 hours | Free Base | 139–140 | 52.6 (52.6 | 4.6 4.6 | 9.85 9.8) |
| 60 | (pyrimidinone) | —Cl | n-BuOH | 4-dimethyl-amino-pyridine | 24 hrs. | Free Base | 135–136 | 52.3 (52.6 | 4.6 4.6 | 9.7 9.8) |
| 61 | (4-methyl-2-methylpyrimidinone) | —NH.NO₂ | n-BuOH | — | 18 hours | Free Base | 147–149 | 53.5 (53.4 | 5.2 4.8 | 9.4 9.6) |
| 62 | (uracil) | —SMe | n-BuOH | — | 72 hours | Free Base | 128–130 | 52.2 (52.6 | 4.7 4.6 | 9.9 9.8) |
| 63 | (pyridine-CONH₂) | —Cl | DMF | — | 24 hours | HCl.½H₂O | 175 | 50.4 (50.5 | 4.5 4.7 | 8.2 8.7) |

EXAMPLE 64

3-{2-[(4-{2,3-Dichlorophenyl}-3-ethoxycarbonyl-5-methoxycarbonyl-6-methyl-1,4-dihydropyrid-2-yl)methoxy]ethylamino}-4-methoxy-1,2,5-thiadiazole-1-oxide

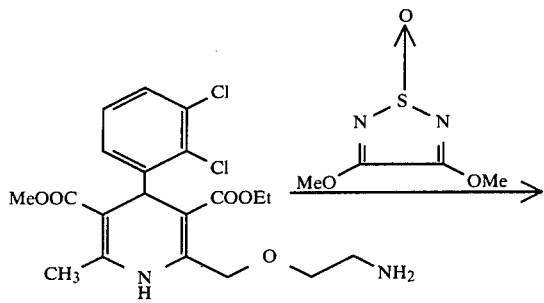

2-[2-Aminoethoxymethyl]-3-ethoxycarbonyl-4-(2,3-dichlorophenyl)-5-methoxycarbonyl-6-methyl-1,4-dihydropyridine (0.5 g) and 3,4-dimethoxy-1,2,5-thiadiazole-1-oxide (0.2 g) were dissolved in methanol (15 ml) and heated at reflux for 14 hours. The solvent was evaporated and the residue chromatographed on silica "Kieselgel 60H" (Trade Mark), eluting with ethyl acetate. The product-containing fractions were combined and evaporated to give an oil which was triturated in ethyl acetate to give the title compound as a solid, yield 0.14 g, m.p. 183°–185°.

Analysis %: Found: C, 48.1; H, 4.6; N, 9.4. Calculated for $C_{23}H_{26}Cl_2N_4O_7S$: C, 48.15; H, 4.55; N, 9.75.

EXAMPLE 65

The following compound, m.p. 158°–160°, was prepared similarly to the previous Example, starting from the corresponding 4-(2-chlorophenyl)-1,4-dihydropyridine and 3,4-dimethoxy-1,2,5-thiadiazole-1-oxide. The reaction time was 18 hours, and the solvent methanol:

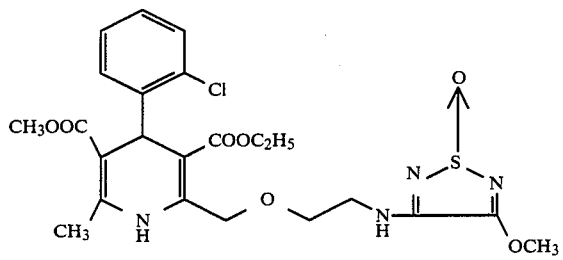

Analysis %: Found: C, 52.0; H, 5.4; N, 10.1. Calculated for $C_{23}H_{27}ClN_4O_7S$: C, 51.25; H, 5.0; N, 10.4.

EXAMPLE 66

The following compound, m.p. 139°–141°, was prepared similarly to Example 64, starting from the corresponding 4-(2-chloro-3-trifluoromethylphenyl)-1,4-dihydropyridine and 3,4-dimethoxy-1,2,5-thiadiazole-1-oxide. The reaction time was 18 hours, and the solvent methanol:

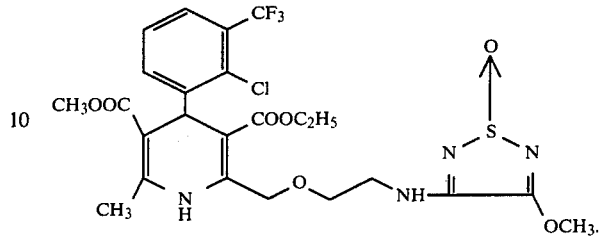

Analysis %: Found: C, 47.3; H, 4.4; N, 9.4. Calculated for $C_{24}H_{26}ClF_3N_4O_7S$: C, 47.5; H, 4.3; N, 9.2.

EXAMPLE 67

3-{2-[(4-{2,3-Dichlorophenyl}-3-ethoxycarbonyl-5-methoxycarbonyl-6-methyl-1,4-dihydropyrid-2-yl)methoxy]ethylamino}-4-amino-1,2,5-thiadiazole-1-oxide hemihydrate

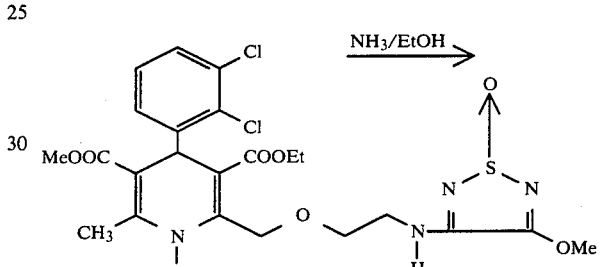

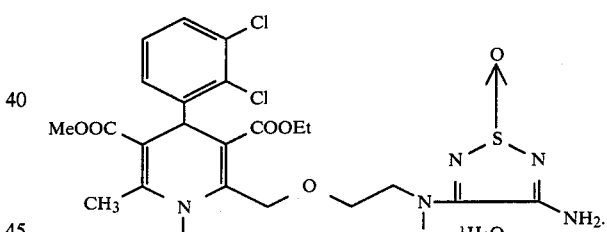

3-{-2-[(4-{2,3-Dichlorophenyl}-3-ethoxycarbonyl-5-methoxycarbonyl-6-methyl-1,4-dihydropyrid-2-yl)methoxy]ethylamino}-4-methoxy-1,2,5-thiadiazole-1-oxide (0.3 g) was dissolved in ethanolic ammonia (10 ml) and stirred at room temperature for 1 hour. The solvent was evaporated and the residue chromatographed on silica "Kieselgel 60H" (Trade Mark), eluting with ethyl acetate. The product containing fractions were combined and evaporated to give an oil which was triturated with ethyl acetate to give the title compound as a solid, yield 0.15 g, m.p. 135°.

Analysis %: Found: C, 46.6; H, 4.6; N, 12.1. Calculated for $C_{22}H_{25}Cl_2N_5O_6S \cdot \frac{1}{2}H_2O$: C, 46.6; H, 4.6; N, 12.3.

EXAMPLE 68

The following compound, m.p. 130°, was prepared similarly to the previous Example, starting from the corresponding 2-chlorophenyl compound and ammonia/EtOH. The reaction time was 1.5 hours:

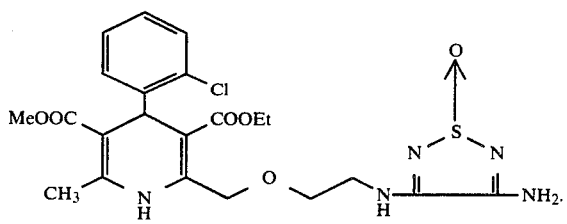

Analysis %: Found: C, 50.4; H, 5.3; N, 13.3. Calculated for $C_{22}H_{26}ClN_5O_6S$: C, 50.4; H, 5.0; N, 13.4.

EXAMPLE 69

The following compound, m.p. 142°–145°, was prepared similarly to Example 67, starting from the corresponding 2-chloro-3-trifluoromethylphenyl compound and ammonia/ethanol. The reaction time was one hour:

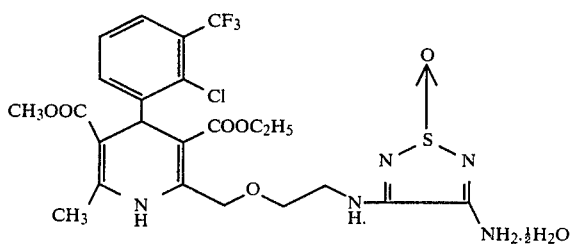

Analysis %: Found: C, 45.6; H, 4.5; N, 11.6. Calculated for $C_{23}H_{25}ClF_3N_5O_6S \cdot \frac{1}{2}H_2O$: C, 46.0; H, 4.4; N, 11.65.

EXAMPLE 70

4-(2-Chlorophenyl)-3-ethoxycarbonyl-5-methoxycarbonyl-6-methyl-2-[2-(2-thiazolin-2-ylamino)ethoxymethyl]-1,4-dihydropyridine

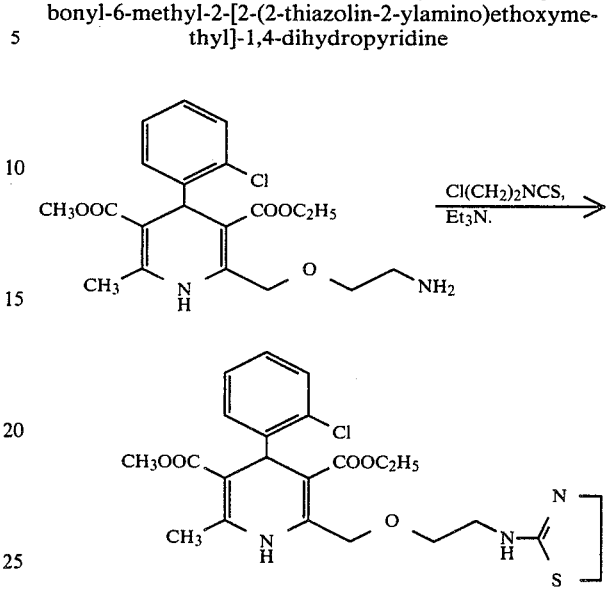

2-[2-Aminoethoxymethyl]-3-ethoxycarbonyl-4-(2-chlorophenyl)-5-methoxycarbonyl-6-methyl-1,4-dihydropyridine (0.5 g), triethylamine (0.3 ml) and 2-chloroethylisothiocyanate (0.16 ml) were dissolved in methylene chloride (5 ml) and the mixture was stirred at room temperature for 2 hours. The mixture was then washed with water (5 ml), dried, filtered and evaporated to give a gum. Chromatography of the gum on silica "Kieselgel 60H" (Trade Mark) eluting initially with toluene then with chloroform with a trace of methanol gave the title compound, which was recrystallised from ether, yield 0.102 g, m.p. 145°–147°.

Analysis %: Found: C, 55.6; H, 5.75; N, 8.3. Calculated for $C_{23}H_{28}ClN_3O_5S$: C, 55.6; H, 5.75; N, 8.3.

EXAMPLE 71

4-(2-Chlorophenyl)-3-ethoxycarbonyl-5-methoxycarbonyl-6-methyl-2-[2-(thiazol-2-ylamino)ethoxymethyl]-1,4-dihydropyridine

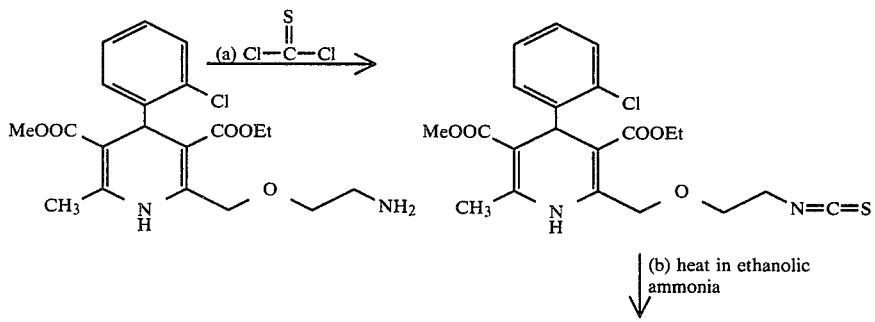

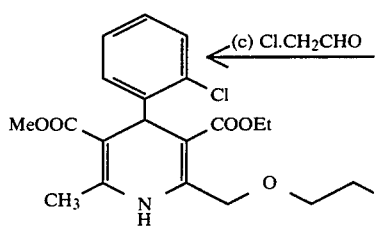
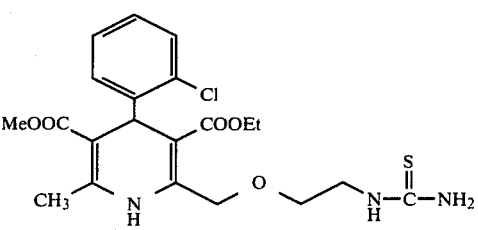

(a) Thiophosgene (0.9 ml) was added to a stirred mixture of 2-(2-aminoethoxymethyl)-3-ethoxycarbonyl-4-(2-chlorophenyl)-5-methoxycarbonyl-6-methyl-1,4-dihydropyridine (4.08 g) and powdered calcium carbonate (3 g) in methylene chloride (25 ml) and water (35 ml). The mixture was stirred overnight at room temperature, filtered, and partitioned between 2N hydrochloric acid and methylene chloride. The organic layer was washed with water, dried ($Na_2CO_3$), filtered and evaporated to give the intermediate isothiocyanate as a solid.

This solid was used directly in the next stage of the reaction without further purification.

(b) The isothiocyanate from part (a) (4 g) was heated in ethanolic ammonia solution for 2½ hours. The resulting precipitate was filtered and recrystallised from ethanol/methylene chloride (5:1) to give the intermediate thiourea, yield 3.8 g, m.p. 203.5°–204.5°.

Analysis %: Found: C, 53.3; H, 5.5; N, 8.6. Calculated for $C_{21}H_{26}N_3ClO_5S$: C, 53.8; H, 5.6; N, 8.9.

(c) The thiourea from part (b) (0.2 g) and chloroacetaldehyde (0.1 g) were dissolved in a 1:1 mixture of chloroform/methanol and the mixture was stirred at room temperature overnight. Removal of the solvent by evaporation left an oil to which toluene (10 ml) was added. After removal of the toluene by evaporation the residue was chromatographed on silica ["Kieselgel 60H" (Trade Mark)]. Elution with toluene, ethyl acetate and finally ethyl acetate/1% methanol afforded a white solid which was recrystallised from ether to give the title compound, yield 0.075 g, m.p. 134°.

Analysis %: Found: C, 56.0; H, 5.4; N, 8.4. Calculated for $C_{23}H_{26}ClN_3O_5S$: C, 56.15; H, 5.3; N, 8.5.

EXAMPLES 72–74

The following compounds were prepared similarly to the method described in part (c) of the previous Example, starting from the same intermediate thiourea and, respectively, $ClCH_2COCH_3$, $BrCH_2COCOOEt$ and $BrCH_2COOEt$.

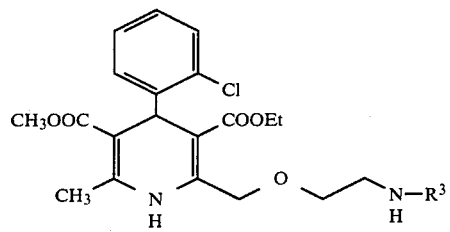

| Example No. | $R^3$ | Reaction Solvent | Reaction Time | m.p. (°C.) | Analysis % (Theoretical in brackets) C | H | N |
|---|---|---|---|---|---|---|---|
| 72 | (N=C(CH₃)–S, thiazole) | 5:1:0.5 $CH_2Cl_2$: MeOH: $Et_3N$ | 3 hrs., reflux temp. | 147° | 56.7 (56.95 | 5.75 5.6 | 8.05 8.3) |
| 73 | (N=C(COOEt)–S, thiazole) | 10:1:0.5 $CHCl_3$: MeOH: $Et_3N$ | 18 hrs., room temp. | 129–131° | 55.3 (55.35 | 5.75 5.35 | 7.15 7.45) |
| 74 | (N=C(=O)–S, thiazole) | 100:1 $CH_2Cl_2$: $Et_3N$ | 12 hrs., room temp. | 160–162° | 54.1 (54.4 | 5.2 5.2 | 8.1 8.3) |

EXAMPLE 75

The following compound, m.p. 190°–192° was prepared similarly to Example 74 but starting from the corresponding 2-chloro-3-trifluoromethyl 1,4-dihydropyridine and without isolation of the intermediates. The reaction time was 20 hours:

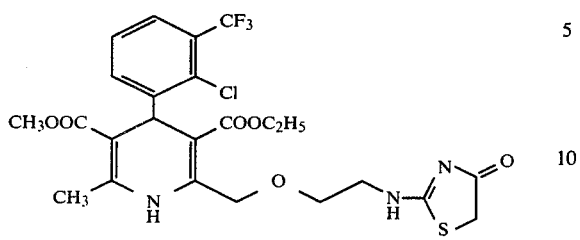

Analysis %: Found: C, 50.1; H, 4.3; N, 7.1. Calculated for C$_{24}$H$_{25}$ClF$_3$N$_3$O$_6$S: C, 50.0; H, 4.4; N, 7.3.

EXAMPLE 76

Preparation of 4-(2,3-Dichlorophenyl)-3-ethoxycarbonyl-5-methoxycarbonyl-6-methyl-2-[2-(4-oxo-2-thiazolin-2-ylamino)ethoxymethyl]-1,4-dihydropyridine

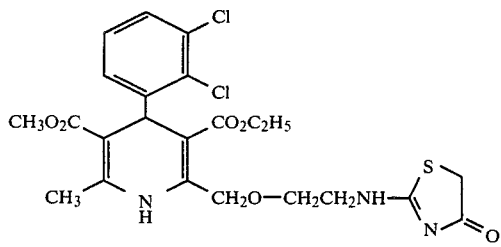

The title compound, m.p. 204°–205°, was prepared by a method similar to that in Example 74 but starting with the corresponding 4-(2,3-dichlorophenyl)1,4-dihydropyridine. The reaction conditions were the same:

Analysis %: Found: C, 51.2; H, 4.7; N, 7.7. Calculated for C$_{23}$H$_{25}$Cl$_2$N$_5$O$_6$S: C, 50.9; H, 4.65; N, 7.75.

EXAMPLE 77

4-(2-Chlorophenyl)-3-ethoxycarbonyl-5-methoxycarbonyl-6-methyl-2-[2-(4-[N-methylcarbamoyl]-thiazol-2-ylamino)ethoxymethyl]-1,4-dihydropyridine

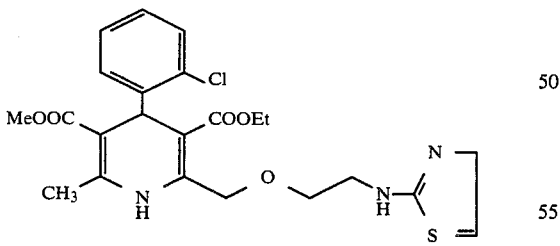

The ester product of Example 73 (0.1 g) was dissolved in a 33% solution of methylamine in ethanol (10 ml) and the mixture was stood at room temperature overnight and then warmed briefly on a steam bath. The solvent was removed by evaporation and the residue chromatographed on silica "Kieselgel 60H" (Trade Mark). Elution with toluene and then 1:2 toluene/ethyl acetate afforded a solid which was recrystallised from ether to give the title compound, yield 52 mg, m.p. 120°.

Analysis %: Found: C, 54.35; H, 5.3; N, 10.2. Calculated for C$_{25}$H$_{29}$ClN$_4$O$_6$S: C, 54.7; H, 5.3; N, 10.2.

EXAMPLE 78

2-[2-(4,5-Dihydro-5-oxo-1,2,4-oxadiazol-3-ylamino)ethoxymethyl]-4-(2,3-dichlorophenyl)-3-ethoxycarbonyl-5-methoxycarbonyl-6-methyl-1,4-dihydropyridine monohydrate

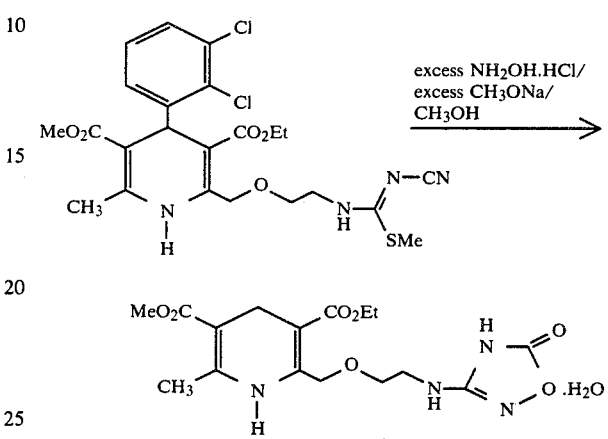

N-{2-[4-{2,3-Dichlorophenyl}-3-ethoxycarbonyl-5-methoxycarbonyl-6-methyl-1,4-dihydropyrid-2-yl]methoxy]ethyl}-N'-cyano-S-methyl-isothiourea (400 mg) was added to a solution of hydroxylamine hydrochloride (57 mg) and sodium methoxide (44 mg) in methanol (10 ml) and heated under reflux for 1 hour. The solution was evaporated to dryness and the residue taken up in ethyl acetate and washed with 2M hydrochloric acid and aqueous sodium carbonate. The organic layer was dried over magnesium sulphate, filtered and evaporated. The residue was chromatographed on "Merck" (Trade Mark) J60 silica eluting with ethyl acetate. The product containing fractions were combined and evaporated to dryness, trituration with ether giving the title compound (70 mg), m.p. 132°–134°.

Analysis %: Found: C, 48.45; H, 4.8; N, 10.3. Calculated for C$_{22}$H$_{24}$Cl$_2$N$_4$O$_7$.H$_2$O: C, 48.3; H, 4.9; N, 10.5.

EXAMPLE 79

2-[2-(2-Methyl-3-{3-methylureido}-2H-1,2,4-triazol-5-ylamino)ethoxymethyl]-4-(2,3-dichlorophenyl)-3-ethoxycarbonyl-5-methoxycarbonyl-6-methyl-1,4-dihydropyridine hydrate

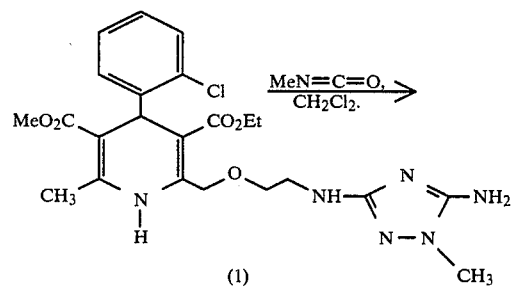

(1)

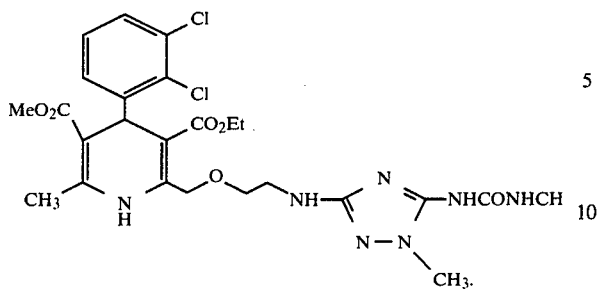

A solution of (1) (0.2 g; product of Example 4) and methyl isocyanate (0.6 ml) in methylene chloride (50 ml) was stirred at room temperature for 18 hours. The solvent was evaporated to dryness and the residue was chromatographed on Merck (Trade Mark) J60 silica eluting with 5% methanol in methylene chloride. The product-containing fractions were combined and evaporated to dryness, trituration with ethyl acetate giving the title compound, yield 0.04 g; m.p. 110°–112°.

Analysis %: Found: C, 51.8; H, 5.9; N, 16.9. Calculated for $C_{25}H_{32}ClN_7O_6 \cdot H_2O$: C, 51.8; H, 5.9; N, 17.1.

EXAMPLE 80

4-(2,3-Dichlorophenyl)-3-ethoxycarbonyl-5-methoxycarbonyl-6-methyl-[2-(6-morpholinopyrimidin-4-ylamino)ethoxymethyl]-1,4-dihydropyridine

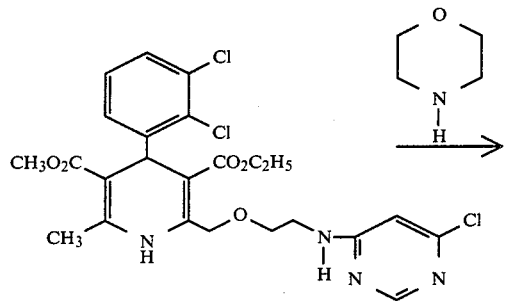

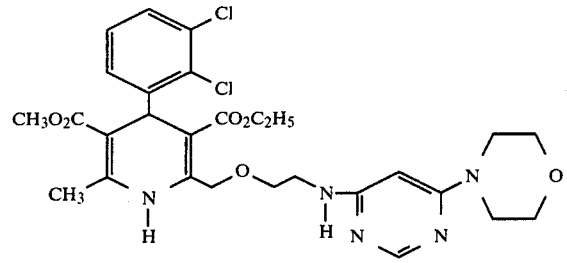

4-(2,3-Dichlorophenyl)-3-ethoxycarbonyl-5-methoxycarbonyl-6-methyl-2-[2-(6-chloropyridin-4-ylamino)ethoxymethyl]-1,4-dihydropyridine (0.5 g) (Product of Example 53) and morpholine (5 ml) were heated together on a steam bath for 18 hours. The excess morpholine was then evaporated and the residue was taken up in ethyl acetate, filtered and chromatographed on silica "Kieselgel 60H" (Trade Mark) eluting with ethyl acetate. The product-containing fractions were combined and evaporated to dryness, trituration with ether giving the title compound (165 mg), m.p. 163°.

Analysis %: Found: C, 55.1; H, 5.5; N, 11.2. Calculated for $C_{28}H_{33}Cl_2N_5O_6$: C, 55.45; H, 5.5; N, 11.55.

EXAMPLES 81–84

The following compounds were prepared similarly to the previous Example, i.e. by the following reaction,

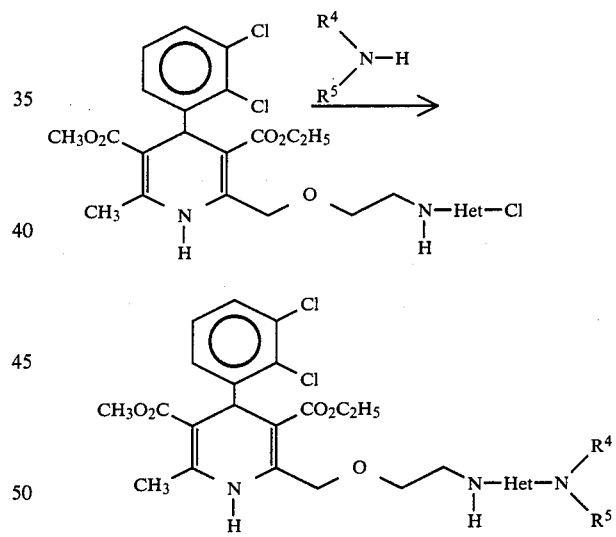

and were characterised in the form indicated:

| Example No. | Het—N(R⁴)(R⁵) | Reaction Solvent | Reaction Time | Form Isolated | m.p. (°C.) | Analysis % (Theoretical in brackets) C | H | N |
|---|---|---|---|---|---|---|---|---|
| 81 | (pyrimidine-N-methylpiperazine group) | — | 18 hours | Free base | 168–170 | 56.5 (56.2 | 5.9 5.9 | 13.4 13.6) |

-continued

| Example No. | Het—N(R⁴)(R⁵) | Reaction Solvent | Reaction Time | Form Isolated | m.p. (°C.) | Analysis % (Theoretical in brackets) C | H | N |
|---|---|---|---|---|---|---|---|---|
| 82 | (piperidine-pyrimidine vinyl structure) | — | 18 hours | Free base | 140–142 | 57.9 (57.6 | 5.7 5.8 | 11.2 11.6) |
| 83 | (N-methylamino pyrimidine vinyl structure) | EtOH | 18 hours | Free base | 158 | 54.2 (54.55 | 5.2 5.3 | 12.8 12.7) |
| 84 | (N-methylamino methylpyrazine structure) | EtOH | 30 hours | Free base | 88–90 | 54.5 (54.55 | 5.55 5.3 | 12.6 12.7) |

EXAMPLES 85–87

The following compounds were prepared similarly to Example 80, i.e. by the following reaction

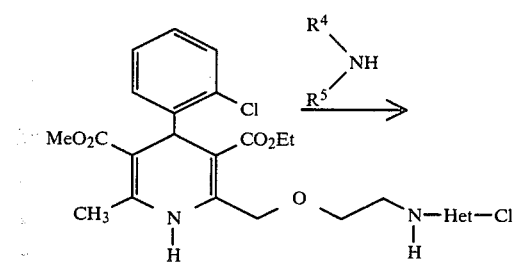

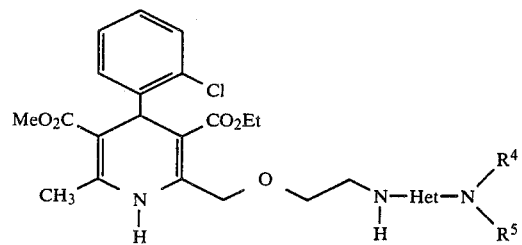

and were characterised in the form indicated:

| Example No. | Het—N(R⁴)(R⁵) | Reaction Solvent | Reaction Time | Form Isolated | m.p. (°C.) | Analysis % (Theoretical in brackets) C | H | N |
|---|---|---|---|---|---|---|---|---|
| 85 | (piperidine-pyrimidine vinyl structure) | — | 18 hours | Hydrate | 147 | 59.4 (59.2 | 6.4 6.5 | 11.8 11.9) |
| 86 | (morpholine-pyrimidine vinyl structure) | — | 20 hours | Hemi-fumarate Hemi-hydrate | 171 | 56.4 (56.3 | 5.8 5.75 | 10.95 11.3) |
| 87 | (morpholino methylpyrazine structure) | — | 18 hours | Free base | 133–134 | 58.45 (58.8 | 6.0 6.0 | 12.4 12.2) |

EXAMPLE 88

4-(2-Chloro-3-trifluoromethylphenyl)-3-ethoxycarbonyl-5-methoxycarbonyl-6-methyl-[2-(6-morpholinopyrimidin-4-ylamino)ethoxymethyl]-1,4-dihydropyridine

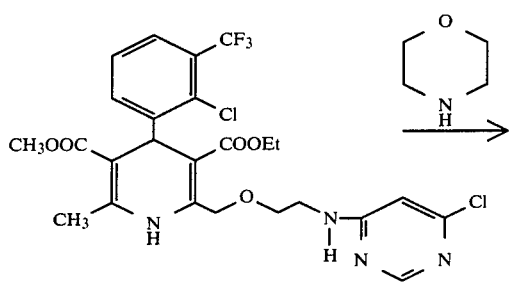

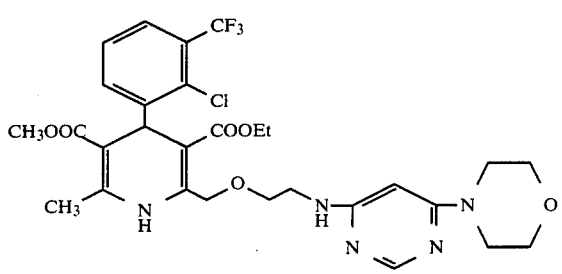

4-(2-Chloro-3-trifluoromethylphenyl)-3-ethoxycarbonyl-5-methoxycarbonyl-6-methyl-2-[2-(6-chloropyrimidin-4-ylamino)ethoxymethyl]-1,4-dihydropyridine was prepared similarly to the procedure of Example 53 from appropriate starting materials and was reacted unpurified with morpholine by a procedure similar to that of Example 80 to give the title compound, m.p. 117°–118°.

Analysis %: Found: C, 54.0; H, 5.6; N, 10.7. Calculated for $C_{29}H_{33}ClF_3N_5O_6$: C, 54.4; H, 5.2; N, 10.9%.

EXAMPLE 89

4-(2,3-Dichlorophenyl)-3-ethoxycarbonyl-5-methoxycarbonyl-6-methyl-2-[2-(pyrazin-2-ylamino)ethoxymethyl]-1,4-dihydropyridine

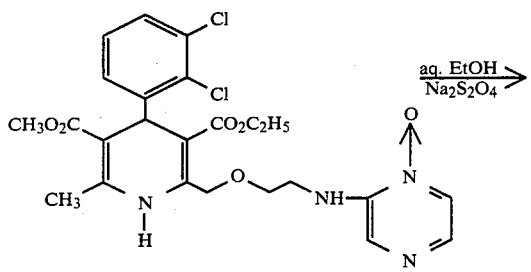

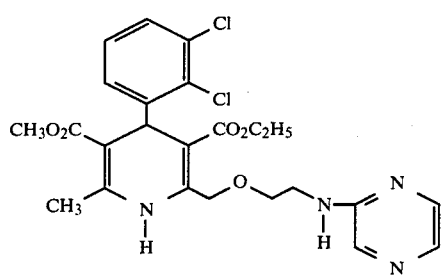

The N-oxide of 4-(2,3-dichlorophenyl)-3-ethoxycarbonyl-5-methoxycarbonyl-6-methyl-2-[2-(pyrazin-2-ylamino)ethoxymethyl]-1,4-dihydropyridine (0.35 g) (product of Example 50) was heated on a steam bath in 50% aqueous ethanol (15 ml), to which was added sodium dithionite (2 g) portionwise over 1.5 hours. The reaction mixture was then heated for a further 1.5 hours before the solvent was evaporated and the residue partitioned between ethyl acetate and water. The organic layer was separated, dried, filtered and evaporated to give an oil. Chromatography on silica "Kiesgel 60H" (Trade Mark) eluting with ether gave an oil which afforded the title compound when triturated with diisopropyl ether, yield 134 mg., m.p. 113°.

Analysis %: Found: C, 55.2; H, 4.9; N, 10.6. Calculated for $C_{24}H_{26}Cl_2N_4O_5$: C, 55.3; H, 5.0; N, 10.75.

EXAMPLE 90

(A.) Preparation of 4-(2,3-Dichlorophenyl)-3-ethoxycarbonyl-2-[2-(3-ethoxycarbonylthioureido)ethoxymethyl]-5-methoxycarbonyl-6-methyl-1,4-dihydropyridine

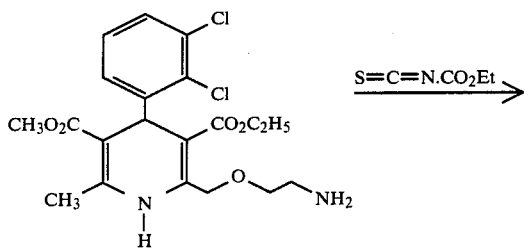

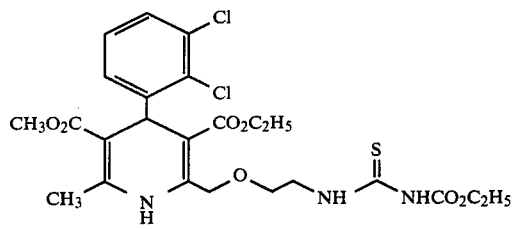

To a suspension of 2-(2-aminoethoxymethyl)-4-(2,3-dichlorophenyl)-3-ethoxycarbonyl-5-methoxycarbonyl-6-methyl-1,4-dihydropyridine (4.43 g) in dry chloroform (50 ml) was added, dropwise, a solution of ethoxycarbonylisothiocyanate (1.31 g) in dry chloroform (25 ml). The reaction was stirred for 18 hours at room temperature before evaporating the solvent and triturating the residue with ether to afford a solid which was recrystallised from diisopropyl ether to give the title compound, yield 2.6 g, m.p. 144°.

Analysis %: Found: C, 50.6; H, 5.2; N, 7.0. Calculated for $C_{24}H_{29}Cl_2N_3O_7S$: C, 50.2; H, 5.1; N, 7.3.

(B.) Preparation of 4-(2,3-Dichlorophenyl)-3-ethoxycarbonyl-2-[2-(5-hydroxy-1H-1,2,4-triazol-3-ylamino)ethoxymethyl]-5-methoxycarbonyl-6-methyl-1,4-dihydropyridine hydrate

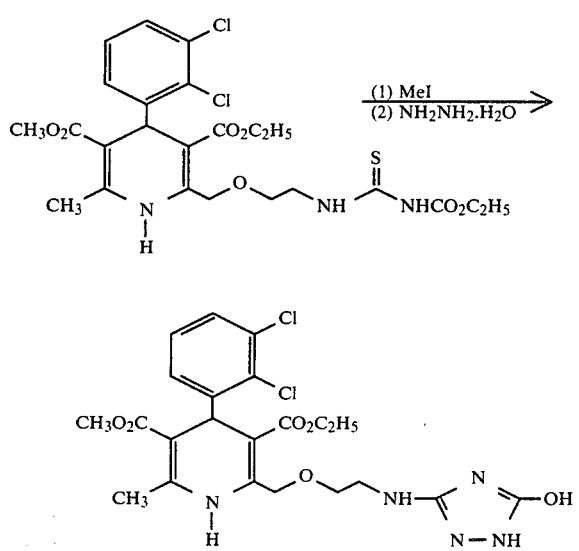

To a suspension of 4-(2,3-dichlorophenyl)-3-ethoxycarbonyl-2-[2-(3-ethoxycarbonylthioureido)ethoxymethyl]-5-methoxycarbonyl-6-methyl-1,4-dihydropyridine (0.25 g) in dry tetrahydrofuran (THF) (5 ml) was added sodium hydride (0.02 g). After stirring for 1 hour at room temperature a solution of methyl iodide (0.07 g) in dry THF (5 ml) was added dropwise and stirring was continued overnight. After evaporation of the solvent, the residue was taken up in methylene chloride and washed (aqueous NaCl), dried (MgSO₄), filtered and evaporated to give a yellow oil (150 mgs).

The oil was dissolved in isopropanol (5 ml) containing hydrazine hydrate (0.06 g) and heated under reflux for 2 days. The solution was then evaporated and the residue taken up in methylene chloride and washed (aqueous NaHCO₃), dried (MgSO₄), filtered and evaporated. The residue was then chromatographed on silica "Kieselgel 60 H" (Trade Mark), eluting with ethyl acetate/methanol (1% increments up to 20% methanol). Product-containing fractions were combined, evaporated and recrystallised from ethyl acetate to afford the title compound, yield 0.048 g, m.pt. 158°.

Analysis %: Found: C, 48.5; H, 4.8; N, 13.0. Calculated for $C_{22}H_{25}Cl_2N_5O_6 \cdot H_2O$: C, 48.5; H, 5.0; N, 12.9.

EXAMPLE 91

(A) Preparation of 4-(2,3-dichlorophenyl)-3-ethoxycarbonyl-2-[2-(5-hydroxy-4-methylpyrimidin-2-ylamino)ethoxymethyl]-5-methoxycarbonyl-6-methyl-1,4-dihydropyridine

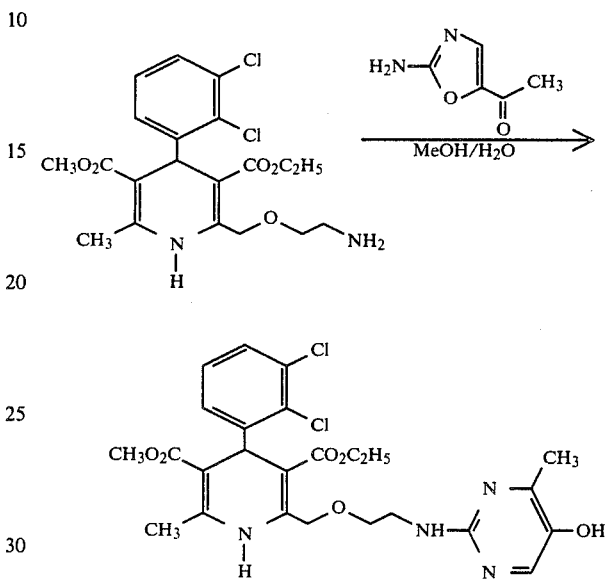

A mixture of 2-(2-aminoethoxymethyl)-3-ethoxycarbonyl-4-2,3-dichlorophenyl)-5-methoxycarbonyl-6-methyl-1,4-dihydropyridine (3.6 g) and 5-acetyl-2-amino-oxazole (0.5 g) in methanol (2 ml) and water (3 ml) was heated on a steam bath for 24 hours. The mixture was then evaporated to dryness and the residue was chromatographed on silica "Kieselgel 60H" (Trade Mark) eluging with ethyl acetate. The product-containing fractions were combined, evaporated and the residue triturated with ether to give the title compound (0.1 g), m.p. 165°.

Analysis %: Found: C, 54.3; H, 5.2; N, 10.2. Calculated for $C_{25}H_{28}Cl_2N_4O_6$: C, 54.45; H, 5.1; N, 10.2%.

(B) Preparation of 2-[2-(4-acetylimidazol-2-ylamino)ethoxymethyl]-4-(2,3-dichlorophenyl)-3-ethoxycarbonyl-5-methoxycarbonyl-6-methyl-1,4-dihydropyridine

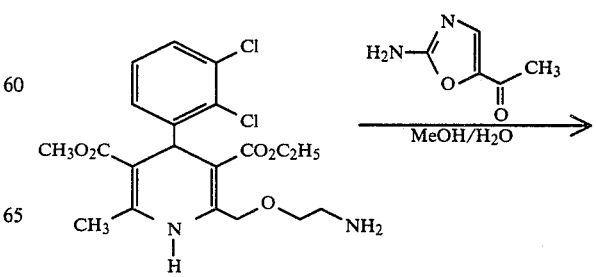

49

-continued

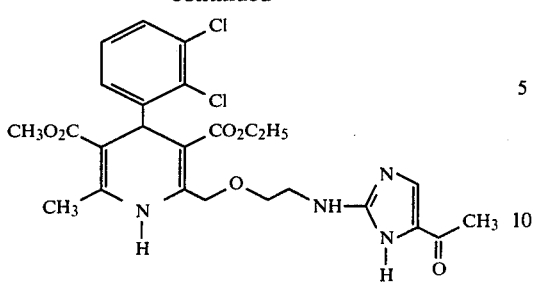

From the same reaction described in Part (A) a second, more polar product was subsequently eluted from the chromatography column using ethyl acetate as the eluent. The fractions containing this second product were combined, evaporated and the residue was redissolved in methylene chloride, washed with dilute hydrochloric acid then with aqueous sodium bicarbonate, dried (MgSO₄), filtered and evaporated. The residue was recrystallised from ethyl acetate to give the title compound (0.14 g), m.p. 177°.

Analysis %: Found: C, 54.6; H, 5.5; N, 9.9. Calculated for $C_{25}H_{28}Cl_2N_4O_6$: C, 54.45; H, 5.1; N, 10.2%.

EXAMPLES 92-97

The following compounds were prepared similarly to the procedure of Example 8, i.e., by the following reaction:

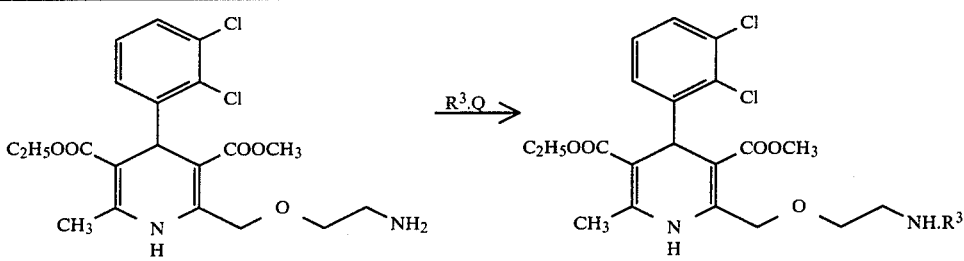

| Example No. | R³ | Q | Reaction Solvent | Base | Reaction Time | Form Isolated | m.p. (°C.) | Analysis % (Theoretical in brackets) | | |
|---|---|---|---|---|---|---|---|---|---|---|
| | | | | | | | | C | H | N |
| 92 | (pyrimidinyl-acetyl) | Cl | nBuOH | 4-dimethyl-amino pyridine | 24 hrs. | Free base hemi-hydrate | 139-141 | 53.15 (52.75 | 5.1 5.0 | 10.6 10.25) |
| 93 | (pyridinyl-acetyl) | Cl | nBuOH | Et₃N | 33 hours | Hemi-fumarate | 197-199 | 52.4 (52.4 | 4.9 4.7 | 9.3 9.4) |
| 94 | (methyl-pyrimidinyl-acetyl) | —NHNO₂ | EtOH | — | 18 hours | Free base sesqui-hydrate | 222 | 51.6 (51.9 | 5.4 5.4 | 9.7 9.4) |
| 95 | (pyrimidinyl-acetyl) | —SMe | EtOH | — | 18 hours | Hydrochloride | 203-205 | (50.0 (50.2 | 4.9 4.7 | 9.9 9.8) |
| 96 | (imidazolinone) | —SMe | EtOH | Et₃N | 17 hours | Hydrochloride hemi-hydrate | 195-198 | 48.5 (48.3 | 4.8 4.9 | 9.85 9.8) |
| 97 | (chloro-pyrimidinyl) | —Cl | EtOH | Et₃N | 50 hours | Free base | 153 | 51.8 (51.9 | 4.6 4.5 | 9.95 10.1) |

EXAMPLES 98–102

The following compounds were prepared similarly to the procedure of the stated Example from appropriate starting materials:

PREPARATION 1

Preparation of 2-[(2-aminoethoxy)methyl]-4-(2-chlorophenyl)-3-ethoxycarbonyl-5-methoxycarbonyl-6-methyl-1,4-dihy-

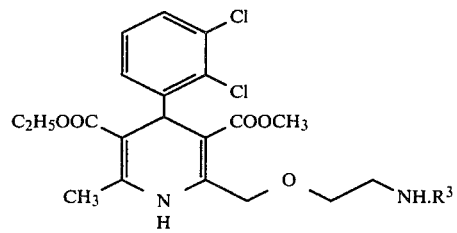

| Example No. | Prepared similarly to the procedure of Example no. | $R^3$ | m.p. (°C.) | Form Isolated | Analysis % (Theoretical in brackets) C | H | N |
|---|---|---|---|---|---|---|---|
| 98 | 74 | (structure) | 194–196 | Free base | 50.7 (50.9 | 4.8 4.65 | 7.7 7.75) |
| 99 | 80 | (structure) | 167–169 | Free base | 55.5 (55.45 | 5.6 5.5 | 11.4 11.55) |
| 100 | 1 | (structure) | 173–175 | Free base hemi-hydrate | 49.3 (49.4 | 5.05 5.1 | 15.5 15.7) |
| 101 | 64 | (structure) | 138–140 | Free base | 48.1 (48.2 | 4.9 4.6 | 9.7 9.8) |
| 102 | 67 | (structure) | 142–144 | Free base hemi-hydrate | 46.35 (46.6 | 4.9 4.6 | 12.3 12.3) | dropyridine maleate

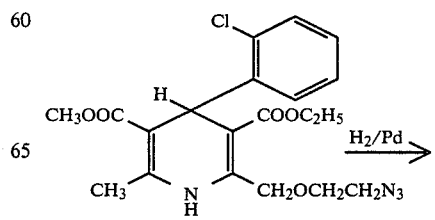

The following Preparations illustrate the preparation of certain starting materials. All temperatures are in °C.:

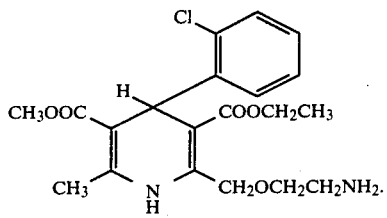

A suspension of 2-(2-azidoethoxymethyl)-4-(2-chlorophenyl)-3-ethoxycarbonyl-5-methoxycarbonyl-6-methyl-1,4-dihydropyridine (103 g) in ethanol (2.5 l) was stirred for 16 hours at room temperature under one atmosphere of hydrogen in the presence of 5% palladium on calcium carbonate (40 g). The reaction mixture was filtered and evaporated and the residue treated with a solution of maleic acid (22 g) in ethanol (100 ml). The reaction mixture was stirred at room temperature for 2 hours and then the resulting solid collected, washed with ethanol, and dried to give the title compound (100 g), m.p. 169°–170.5°.

Analysis %: Found: C, 54.82; H, 5.62; N, 5.46. $C_{24}H_{29}ClN_2O_9$ requires: C, 54.91; H, 5.57; N, 5.34.

PREPARATION 2

2-[2-Aminoethoxymethyl]-4-[2,3-dichlorophenyl]-3-ethoxycarbonyl-5-methoxycarbonyl-6-methyl-1,4-dihydropyridine, m.p. 171°–3°, was prepared similarly to the previous preparation from the appropriate azido compound, and was characterised as the hemifumarate hemihydrate.

Analysis %: Found: C, 51.7; H, 5.3; N, 5.5. Calculated for $C_{20}H_{24}Cl_2N_2O_5 \cdot \frac{1}{2}C_4H_4O_4 \cdot \frac{1}{2}H_2O$: C, 51.8; H, 5.3; N, 5.5.

The hemifumarate was neutralised to the free base form, m.p. 120°–122°.

PREPARATION 3

2-(2-Azidoethoxymethyl)-4-(2-chlorophenyl)-3-ethoxycarbonyl-5-methoxycarbonyl-6-methyl-1,4-dihydropyridine A solution of 2-azidoethanol (160 g) in tetrahydrofuran (300 ml) was added over 40 minutes to a suspension of sodium hydride (114 g; 80% dispersion in oil) in tetrahydrofuran (500 ml). The mixture was stirred at room temperature for 1 hour and the ice-cooled solution treated with a solution of ethyl 4-chloroacetoacetate (276 g) in tetrahydrofuran (250 ml) dropwise over 2 hours. The mixture was stirred at room temperature for 16 hours, diluted with ethanol (150 ml), and the pH adjusted to 6-7 with 4M hydrochloric acid. Sufficient water was added to dissolve the solid present and the layers were separated. The organic layer was evaporated and the residue diluted with water (600 ml) and evaporated. The residue was partitioned between ethyl acetate and water and the aqueous layer extracted twice with ethyl acetate. The combined ethyl acetate extracts were dried (MgSO₄) and evaporated to give ethyl 4-(2-azidoethoxy)acetoacetate as a brown oil, which was shown by g.l.c. to be 73% pure. A mixture of this crude product and ammonium acetate (92.3 g) in ethanol (600 ml) was heated under reflux for 1 hour, allowed to cool to room temperature, and treated with methyl 2-(2-chlorobenzylidene) acetoacetate (286.6 g). The mixture was heated under reflux for 5.5 hours and then evaporated. The residue was stirred with methanol (1.5 l) for 16 hours and the resulting solid collected, washed twice with methanol, dried, and recrystallised from methanol to give the title compound (78 g), m.p. 145°–146°.

Analysis %: Found: C, 55.39; H, 5.37; N, 13.01. Calculated for $C_{20}H_{23}ClN_4O_5$: C, 55.23; H, 5.33; N, 12.88.

PREPARATION 4

2-(2-Azidoethoxy)methyl-4-(2,3-dichlorophenyl)-3-ethoxycarbonyl-5-methoxycarbonyl-6-methyl-1,4-dihydropyrine was prepared by the method described in Preparation 3 using methyl 2-(2,3-dichlorobenzylidene)acetoacetate instead of methyl 2-(2-chlorobenzylidene)acetoacetate. The product had an m.p. of 141°.

Analysis %: Found: C, 50.88; H, 4.78; N, 11.73. Calculated for $C_{20}H_{22}Cl_2N_4O_5$: C, 51.18; H, 4.73; N, 11.94.

PREPARATION 5

(i) Preparation of Ethyl-4-(2-phthalimidoethoxy)acetoacetate

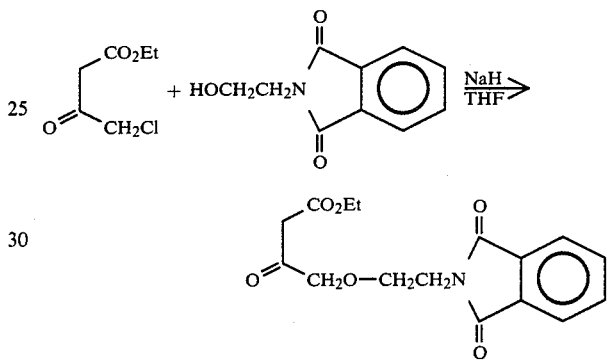

To a slurry of sodium hydride (57% dispersion in oil, 66.1 g; 1.57M), in tetrahydrofuran (500 ml) cooled to 0° under nitrogen was added B 2-phthalimidoethanol (150 g; 0.785M) followed by ethyl 4-chloroacetoacetate (129 g; 0.785M) in tetrahydrofuran (250 ml) over 1 hour. The mixture was stirred at room temperature overnight then poured into a mixture of 1M hydrochloric acid (800 ml) and ethyl acetate (750 ml). The organic phase was separated and the solvent was evaporated at reduced pressure. The residue separated into two layers and the upper layer of mineral oil was removed to leave the title compound (243 g) as a crude product which was used without further purification.

(ii) Preparation of 4-(2-chlorophenyl)-3-ethoxycarbonyl-5-methoxycarbonyl-6-methyl-2-[2-phthalimidoethoxymethyl]-1,4-dihydropyridine

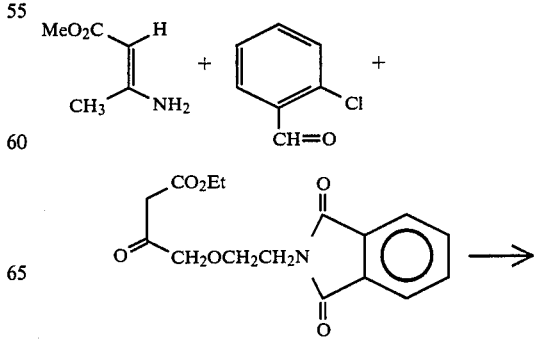

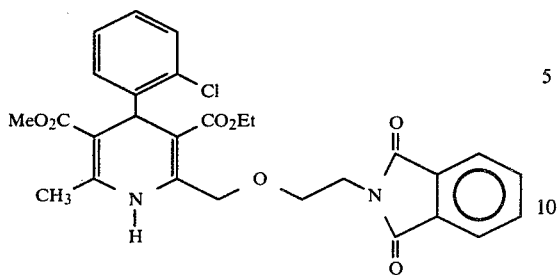

Methyl 3-aminocrotonate (72.2 g; 0.627M) and 2-chlorobenzaldehyde (88.1 g; 0.627M) were added to a solution of ethyl 4-(2-phthalimidoethoxy)acetoacetate (200 g; 0.627M) in isopropanol (1 liter) and the mixture was heated under reflux for 20 hours. The isopropanol was evaporated under reduced pressure and replaced by acetic acid (1 liter). After granulation at 10° the solid was collected and slurried in methanol (300 ml). The solid was collected by filtration and dried in vacuo at 50° to afford the title compound, yield 84.4 g, m.p. 146°–147°.

Analysis %: Found: C, 62.2; H, 5.0; N, 5.2. Calculated for $C_{28}H_{27}ClN_2O_7$: C, 62.4; H, 5.05; N, 5.2.

PREPARATION 6

The following compound, m.p. 148°–150°, was prepared similarly to the previous Preparation but using the corresponding 2,3-dichlorobenzaldehyde. The reaction time was the same:

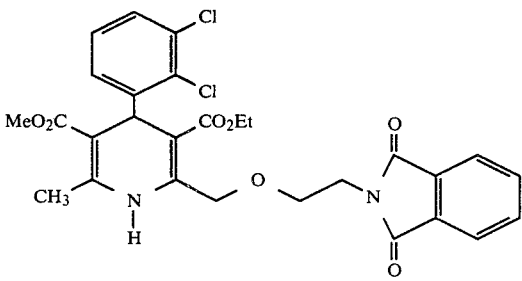

Analysis %: Found: C, 58.7; H, 4.5; N, 5.0. Calculated for $C_{28}H_{26}Cl_2N_2O_7$: C, 58.6; H, 4.6; N, 4.9.

PREPARATION 7

Preparation of 2-(2-aminoethoxymethyl)-4-(2-chlorophenyl)-3-ethoxycarbonyl-5-methoxycarbonyl-1,4-dihydropyridine maleate

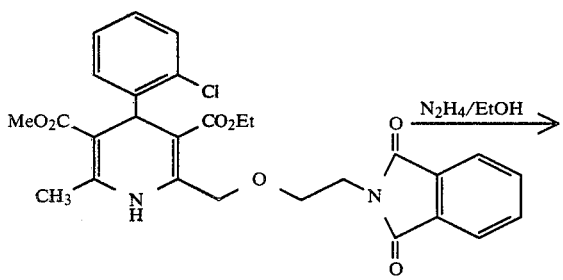

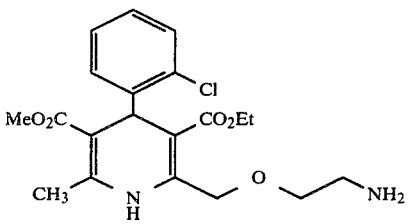

The intermediate phthalimido compound from Preparation 5 (400 g) was suspended in ethanol (6 liters) containing hydrazine hydrate (111 g) and heated under reflux for 2 hours. After cooling the reaction mixture was filtered and the filtrate was evaporated to give a yellow oil. The oil was taken up in methylene chloride (6.5 liters), washed ($H_2O$), dried ($MgSO_4$) and evaporated. The residue was taken up in hot methylated spirit (1.2 liters) and diluted with hot methylated spirit (400 ml) containing maleic acid (86 g). After cooling the title compound crystallised out as its maleate salt, yield 303 g, m.p. 169°–171°.

Analysis %: Found: C, 54.8; H, 5.55; N, 5.3. Calculated for $C_{20}H_{25}ClN_2O_5 \cdot C_4H_4O_4$: C, 54.9; H, 5.6; N, 5.3.

PREPARATION 8

The following compound, m.p. 171°–173° was prepared similarly to the previous preparation but starting from the corresponding 2,3-dichlorophenyl compound:

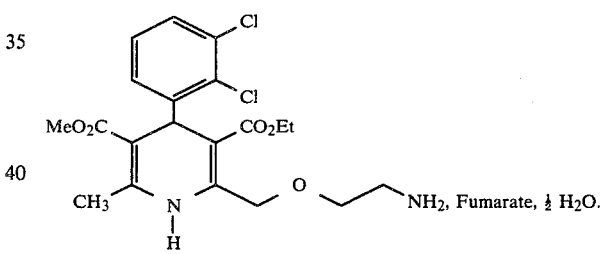

Analysis %: Found: C, 51.55; H, 5.3; N, 5.4. Calculated for $C_{20}H_{24}Cl_2N_2O_5 \cdot C_4H_4O_4 \cdot \frac{1}{2}H_2O$: C, 51.5; H, 5.05; N, 5.0.

PREPARATION 9

The following compound, m.p. 179°, was prepared similarly to Preparation 5 but using the corresponding 2-chloro-3-trifluoromethylbenzaldehyde in stage (ii). The reaction time was the same:

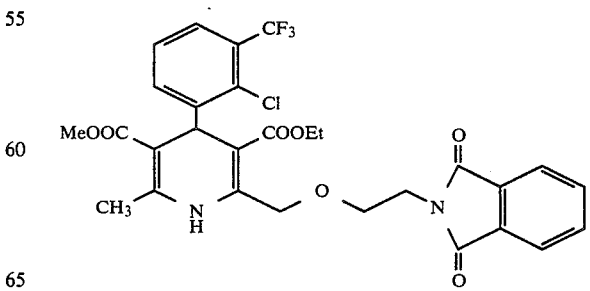

Analysis %: Found: C, 57.2; H, 4.45; N, 4.8. Calculated for $C_{29}H_{26}ClF_3N_2O_7$: C, 57.4; H, 4.3; N, 4.6.

PREPARATION 10

Preparation of
2-(2-Azidoethoxymethyl)-4-(2-chloro-3-trifluoromethylphenyl)-3-ethoxycarbonyl-5-methoxycarbonyl-6-methyl-1,4-dihydropyridine

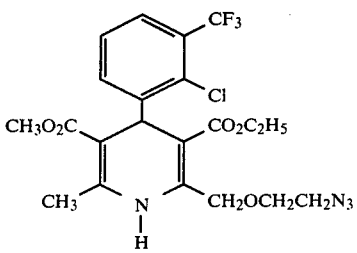

The title compound, m.p. 143°–145°, was prepared similarly to the method described in Preparation 3 but using the corresponding 2-chloro-3-trifluoromethylbenzaldehyde. The reaction time was the same:
Analysis %: Found: C, 50.2; H, 4.4; N, 11.3. Calculated for $C_{21}H_{22}ClF_3N_4O_5$: C, 50.15; H, 4.4; N, 11.1.

PREPARATION 11

Preparation of
2-[2-Aminoethoxymethyl]-4-(2-chloro-3-trifluoromethylphenyl)-3-ethoxycarbonyl-5-methoxycarbonyl-6-methyl-1,4-dihydropyridine

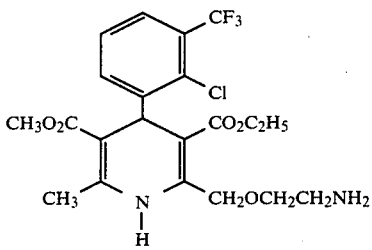

The title compound was prepared by the catalytic hydrogenation of the azido compound of Preparation 10 by the method described in Preparation 1. This compound was confirmed by n.m.r. and i.r. analysis to be identical to the product of Preparation 13.

PREPARATION 12

Preparation of
2-(2-Azidoethoxymethyl)-4-(2,3-dichlorophenyl)-3-methoxycarbonyl-5-ethoxycarbonyl-6-methyl-1,4-dihydropyridine

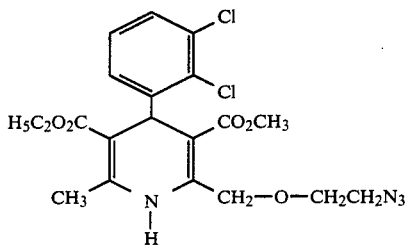

The title compound, m.p. 126°, was prepared similarly to the method described in Preparation 3 but using methyl 4-bromoacetoacetate instead of ethyl 4-chloroacetoacetate yielding methyl 4-(2-azidoethoxy)acetoacetate instead of ethyl 4-(2-azidoethoxy)acetoacetate. The other conditions were the same:
Analysis %: Found: C, 51.3; H, 4.7; N, 12.1. Calculated for $C_{20}H_{22}Cl_2N_4O_5$: C, 51.2; H, 4.7; N, 11.9.

PREPARATION 13

Preparation of
2-(2-aminoethoxymethyl)-4-(2-chloro-3-trifluoromethylphenyl)-3-ethoxycarbonyl-5-methoxycarbonyl-6-methyl-1,4-dihydropyridine

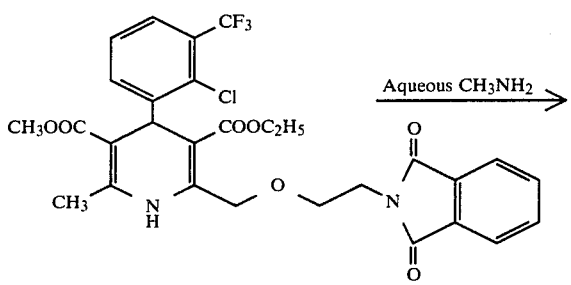

The intermediate phthalimido compound from Preparation 9 (2.8 g) was added to aqueous methylamine (14 ml of 40%) and stirred at room temperature for 17 hours. The resultant solid was filtered, redissolved in chloroform (50 ml), dried ($MgSO_4$), filtered and evaporated to give a yellow solid. Crystallisation from hexane gave the title compound, yield 1.0 g, m.p. 122°.
Analysis %: Found: C, 53.25; H, 4.9; N, 5.75. Calculated for $C_{21}H_{24}ClF_3N_2O_5$: C, 52.9; H, 5.1; N, 5.9.

PREPARATION 14

Preparation of
4-(2,3-dichlorophenyl)-5-ethoxycarbonyl-3-methoxycarbonyl-6-methyl-2-[2-phthalimidoethoxymethyl]-1,4-dihydropyridine

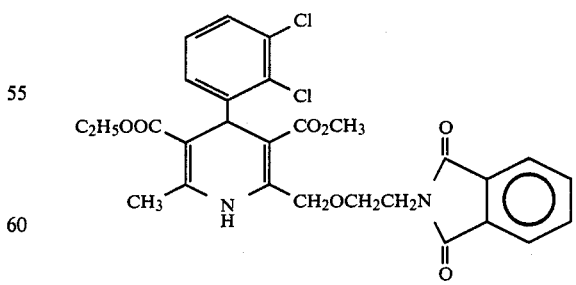

The title compound, m.p. 165°, was prepared similarly to the method described in Preparation 5(ii) but using 2,3-dichlorobenzaldehyde, methyl 4-(2-phthalimidoethoxy)-acetoacetate and ethyl 3-aminocrotonate. The reaction time was the same:

Analysis %: Found: C, 58.5; H, 4.7; N, 5.0. Calculated for $C_{28}H_{26}Cl_2N_2O_7$: C, 58.65; H, 4.6; N, 4.9.

The starting acetoacetate was prepared similarly to Preparation 5(i).

PREPARATION 15

Preparation of 2-(2-aminoethoxymethyl)-4-(2,3-dichlorophenyl)-5-ethoxycarbonyl-6-methyl-3-methoxycarbonyl-1,4-dihydropyridine

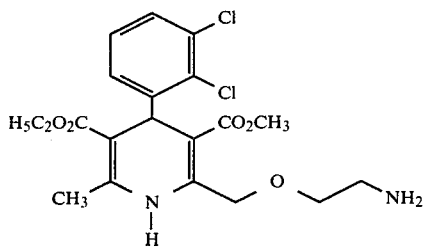

The title compound, m.p. 131°–132°, was prepared similarly to the method described in Preparation 13 but using the material from Preparation 14.

Analysis %: Found: C, 53.9; H, 5.5; N, 6.4. Calculated for $C_{20}H_{24}Cl_2N_2O_5$: C, 54.2; H, 5.5; N, 6.3.

PREPARATION 16

Preparation of 2-chloro-3-trifluoromethylbenzaldehyde

2-Chloro-1-trifluoromethylbenzene (54.15 g) was dissolved in dry tetrahydrofuran (500 ml) and stirred while cooling to −68° under a stream of dry nitrogen. (The whole reaction is carried out under dry nitrogen until the addition of distilled water.) To this was added n-butyl lithium (180 ml of a 1.6M solution in hexane) dropwise keeping the temperature below −60°. After stirring at −68° for a further 2 hours, a solution of dimethylformamide (22 ml) in dry tetrahydrofuran (100 ml) was added dropwise keeping the temperature below −60°. The reaction mixture was allowed to warm to room temperature slowly over 17 hours and distilled water (200 ml) was then added. The organic phase was separated off and the aqueous liquors were extracted with ether (100 ml). The combined ether extracts plus the organic phase were washed with saturated brine, dried (MgSO₄), filtered and evaporated to give 61.5 g of an orange oil, being the crude title compound.

This oil was then added to an aqueous sodium bisulphite solution (65 g in 600 ml distilled water) and heated at 60° for 0.5 hours. The solution was extracted with methylene chloride (3×100 ml) and, after acidification of the aqueous phase with concentrated sulphuric acid to pH1, was heated at 100° for a further 0.5 hours. The resultant aqueous solution was extracted with methylene chloride (3×200 ml) and the combined organic extracts were dried (MgSO₄), filtered and evaporated to give 42 g of a colourless solid which was crystallised from hexane to give the title compound, m.p. 43°–44°.

Analysis %: Found: C, 45.9; H, 2.0. Calculated for $C_8H_4F_3ClO$: C, 46.1; H, 2.0.

PREPARATION 17

Preparation of 2,3-dichlorobenzaldehyde

A similar route to that described in the previous Preparation, starting from 1,2-dichlorobenzene, proved to be a superior method for preparing the title compound, m.p. 62°.

Analysis %: Found: C, 47.62; H, 2.38. Calculated for $C_7H_4Cl_2O$: C, 48.04; H, 2.30.

ACTIVITY DATA

The molar concentrations of the compounds required to reduce the response by 50% in the test specified on pages 16–17 are given below (1M=1 gm.Mole/liter). The smaller the concentration the more active the compound.

| Compound | $IC_{50}$ |
|---|---|
| Product of Example 1B | $2 \times 10^{-8}$ M |
| Product of Example 2 | $2.29 \times 10^{-9}$ M |
| Product of Example 3B | $6.02 \times 10^{-9}$ M |
| Product of Example 4 | $8.12 \times 10^{-9}$ M |
| Product of Example 5 | $3.02 \times 10^{-9}$ M |
| Product of Example 6 | $1.15 \times 10^{-8}$ M |
| Product of Example 7 | $3.47 \times 10^{-9}$ M |
| Product of Example 8 | $1.05 \times 10^{-8}$ M |
| Product of Example 9 | $1.26 \times 10^{-8}$ M |
| Product of Example 10 | $1.9 \times 10^{-9}$ M |
| Product of Example 11 | $4.26 \times 10^{-7}$ M |
| Product of Example 12 | $2.88 \times 10^{-8}$ M |
| Product of Example 13 | $6.3 \times 10^{-9}$ M |
| Product of Example 14 | $1.0 \times 10^{-8}$ M |
| Product of Example 15 | $5.01 \times 10^{-8}$ M |
| Product of Example 16 | $1.00 \times 10^{-7}$ M |
| Product of Example 17 | $1.31 \times 10^{-8}$ M |
| Product of Example 18 | $3.16 \times 10^{-8}$ M |
| Product of Example 19 | $1.00 \times 10^{-8}$ M |
| Product of Example 20 | $1.00 \times 10^{-7}$ M |
| Product of Example 21 | $1.00 \times 10^{-7}$ M |
| Product of Example 22 | $1.82 \times 10^{-8}$ M |
| Product of Example 23 | $1.00 \times 10^{-7}$ M |
| Product of Example 24 | $1.00 \times 10^{-8}$ M |
| Product of Example 25 | $4.57 \times 10^{-8}$ M |
| Product of Example 26 | $3.71 \times 10^{-9}$ M |
| Product of Example 27 | $3.98 \times 10^{-9}$ M |
| Product of Example 28 | $1.31 \times 10^{-8}$ M |
| Product of Example 29 | $1.81 \times 10^{-8}$ M |
| Product of Example 30 | $2.34 \times 10^{-9}$ M |
| Product of Example 31 | $1.77 \times 10^{-8}$ M |
| Product of Example 32 | $1.58 \times 10^{-8}$ M |
| Product of Example 33 | $6.30 \times 10^{-9}$ M |
| Product of Example 34 | $1.31 \times 10^{-8}$ M |
| Product of Example 35 | $5.75 \times 10^{-9}$ M |
| Product of Example 36 | $3.16 \times 10^{-9}$ M |
| Product of Example 37 | $1.00 \times 10^{-8}$ M |
| Product of Example 38 | $2.51 \times 10^{-8}$ M |
| Product of Example 39 | $2.69 \times 10^{-9}$ M |
| Product of Example 40 | $2.23 \times 10^{-9}$ M |
| Product of Example 41 | $7.76 \times 10^{-10}$ M |
| Product of Example 42 | $4.16 \times 10^{-9}$ M |
| Product of Example 43 | $8.31 \times 10^{-9}$ M |
| Product of Example 44 | $1.58 \times 10^{-8}$ M |
| Product of Example 45 | $1.09 \times 10^{-9}$ M |
| Product of Example 46 | $3.01 \times 10^{-9}$ M |
| Product of Example 47 | $1.25 \times 10^{-9}$ M |
| Product of Example 48 | $2.95 \times 10^{-8}$ M |
| Product of Example 49 | $3.98 \times 10^{-9}$ M |
| Product of Example 50 | $1.34 \times 10^{-9}$ M |
| Product of Example 51 | $2.51 \times 10^{-9}$ M |
| Product of Example 52 | $6.02 \times 10^{-9}$ M |
| Product of Example 53 | $3.16 \times 10^{-6}$ M |
| Product of Example 54 | $1.20 \times 10^{-9}$ M |
| Product of Example 59 | $3.72 \times 10^{-9}$ M |
| Product of Example 60 | $4.47 \times 10^{-8}$ M |
| Product of Example 61 | $2.24 \times 10^{-9}$ M |
| Product of Example 62 | $1.35 \times 10^{-9}$ M |
| Product of Example 63 | $2.95 \times 10^{-9}$ M |
| Product of Example 64 | $1.00 \times 10^{-8}$ M |
| Product of Example 65 | $2.51 \times 10^{-8}$ M |
| Product of Example 66 | $2.24 \times 10^{-9}$ M |
| Product of Example 67 | $1.99 \times 10^{-8}$ M |
| Product of Example 68 | $1.31 \times 10^{-8}$ M |
| Product of Example 70 | $9.33 \times 10^{-9}$ M |
| Product of Example 71 | $1.00 \times 10^{-8}$ M |
| Product of Example 72 | $3.98 \times 10^{-8}$ M |

-continued

| Compound | IC$_{50}$ |
|---|---|
| Product of Example 73 | 4.4 × 10$^{-9}$ M |
| Product of Example 74 | 2.00 × 10$^{-8}$ M |
| Product of Example 75 | 7.08 × 10$^{-9}$ M |
| Product of Example 77 | 5.37 × 10$^{-9}$ M |
| Product of Example 78 | 2.29 × 10$^{-9}$ M |
| Product of Example 79 | 6.60 × 10$^{-9}$ M |
| Product of Example 80 | 1.34 × 10$^{-9}$ M |
| Product of Example 81 | 3.16 × 10$^{-9}$ M |
| Product of Example 82 | 4.07 × 10$^{-9}$ M |
| Product of Example 83 | 3.16 × 10$^{-9}$ M |
| Product of Example 84 | 5.01 × 10$^{-9}$ M |
| Product of Example 85 | 5.01 × 10$^{-9}$ M |
| Product of Example 86 | 1.58 × 10$^{-9}$ M |
| Product of Example 87 | 1.00 × 10$^{-7}$ M |
| Product of Example 88 | 1.26 × 10$^{-10}$ M |
| Product of Example 89 | 5.01 × 10$^{-10}$ M |
| Product of Example 90B | 1.00 × 10$^{-8}$ M |
| Product of Example 91A | 1.00 × 10$^{-9}$ M |
| Product of Example 91B | 2.5 × 10$^{-9}$ M |

We claim:

1. A dihydropyridine compound of the formula

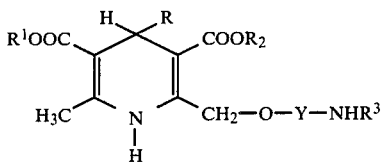

or a pharmaceutically acceptable acid addition salt thereof, wherein:

R is phenyl; phenyl substituted independently by one or two of nitro, halo, C$_1$-C$_4$ alkyl, C$_1$-C$_4$ alkoxy, hydroxy, trifluoromethyl or cyano; 1-naphthyl; or 2-naphthyl;

R$^1$ and R$^2$ are each independently C$_1$-C$_4$ alkyl or 2-methoxyethyl;

R$^3$ is a 5-membered heterocyclic azole containing three hetero atoms; or a substituted 5-membered heterocyclic azole containing three hetero atoms; with the proviso that R$^3$ is attached to the adjacent nitrogen atom by means of a bond between a carbon atom of R$^3$ and the adjacent nitrogen atom; and Y is alkylene or alkylene substituted by 1 or 2 methyl groups wherein alkylene in each instance has 2-4 carbon atoms; wherein the substituted 5-membered heterocyclic is substituted by C$_1$-C$_4$ alkyl, C$_1$-C$_4$ alkoxy, halo, hydroxy, oxo, cyano, 3-(C$_1$-C$_4$ alkyl) ureido, phenyl, phenoxy, pyridyl, acetyl, (C$_1$-C$_4$ alkoxy) carbonyl, —NR$^4$R$^5$, —SO$_2$NR$^4$R$^5$ or —CONR$^4$R$^5$ where R$^4$ and R$^5$ are each independently hydrogen or C$_1$-C$_4$ alkyl.

2. A compound according to claim 1 wherein R is phenyl substituted by 1 or 2 of halo or trifluoromethyl.

3. A compound according to claim 2 wherein R is 2-chlorophenyl, 2,3-dichlorophenyl or 2-chloro-3-(trifluoromethyl)-phenyl.

4. A compound according to claim 3 wherein Y is ethylene and R$^1$ is methyl and R$^2$ is ethyl or R$^1$ is ethyl and R$^2$ is methyl.

5. A compound according to claim 4 wherein R$^3$ is a 5-membered heterocyclic azole containing one nitrogen and two further heteroatoms or moieties each independently selected from the group consisting of oxygen, sulfur, sulfoxide, nitrogen, or nitroxide; said 5-membered heterocyclic azole substituted by C$_1$-C$_4$ alkyl, C$_1$-C$_4$ alkoxy, halo, hydroxy, oxo, cyano, 3-(C$_1$-C$_4$ alkyl)ureido, phenyl, phenoxy, pyridyl, acetyl, (C$_1$-C$_4$ alkoxy)carbonyl, —NR$^4$R$^5$, —SO$_2$NR$^4$R$^5$ or —CONR$^4$R$^5$ where R$^4$ and R$^5$ are each independently hydrogen or C$_1$-C$_4$ alkyl.

6. A compound as claimed in claim 5 wherein R$^3$ is a 5-membered heterocyclic azole, or the N- or S-oxide thereof, selected from the group consisting of triazolyl, oxadiazolyl, thiadiazolyl; or the heterocyclic azole, or the N- or S-oxide thereof, substituted by C$_1$-C$_4$ alkyl, C$_1$-C$_4$ alkoxy, halo, hydroxy, oxo, cyano, 3-methylureido, phenyl, phenoxy, pyridyl, acetyl, carbamoyl, N-methylcarbamoyl, (C$_1$-C$_4$ alkoxy)carbonyl, —NR$^4$R$^5$ or —SO$_2$NR$^4$R$^5$, where R$^4$ and R$^5$ are each independently hydrogen or C$_1$-C$_4$ alkyl.

7. A compound according to claim 6 wherein R$^3$ is

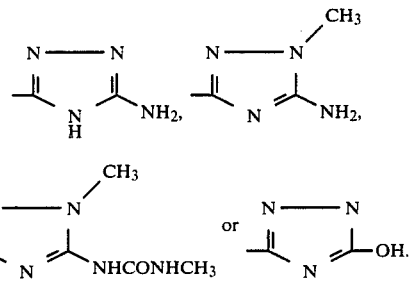

8. A compound according to claim 6 wherein R$^3$ is

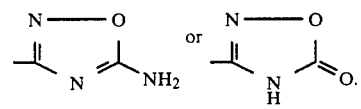

9. A compound according to claim 6 wherein R$^3$ is

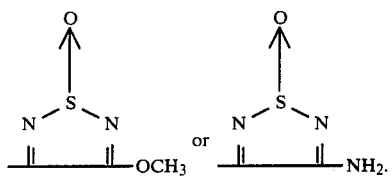

10. A compound according to claim 1, wherein R$^1$ is CH$_3$, R$^2$ is C$_2$H$_5$, Y is ethylene, R is 2,3-dichlorophenyl, and R$^3$ is

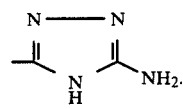

11. A method of treating hypertension in an animal in need of such treatment comprising the step of administering to said animal an antihypertensive effective amount of a compound of claim 1.

12. A pharmaceutical composition comprising an antihypertensive, anti-ischaemic or angina-alleviating effective amount of a compound of claim 1 and a pharmaceutically acceptable diluent or carrier.

13. A method of treating ischaemia in an animal in need of such treatment comprising the step of administering to said animal an anti-ischaemic effective amount of a compound according to claim 1.

14. A method of treating angina in an animal in need of such treatment comprising the step of administering to said animal an angina-alleviating effective amount of the compound of claim 1.

* * * * *